(12) United States Patent
Lahey et al.

(10) Patent No.: US 6,774,142 B2
(45) Date of Patent: Aug. 10, 2004

(54) INHIBITION BY 3-DEOXYFLAVONOIDS OF T-LYMPHOCYTE ACTIVATION AND THERAPIES RELATED THERETO

(76) Inventors: Thomas P. Lahey, 8 Pacific Crest, Laguna Niguel, CA (US) 92677; Vithal J. Rajadhyasksha, 27436 Esquina, Mission Viejo, CA (US) 92691

( * ) Notice: Subject to any disclaimer, the term of this patent is extended or adjusted under 35 U.S.C. 154(b) by 0 days.

(21) Appl. No.: 10/236,861

(22) Filed: Sep. 6, 2002

(65) Prior Publication Data

US 2003/0069192 A1 Apr. 10, 2003

Related U.S. Application Data

(60) Provisional application No. 60/407,125, filed on Aug. 30, 2002, and provisional application No. 60/317,666, filed on Sep. 6, 2001.

(51) Int. Cl.$^7$ ............................................. A61K 31/335
(52) U.S. Cl. ........................ 514/456; 514/100; 514/455; 549/220; 549/387; 549/403
(58) Field of Search ................................ 549/387, 403, 549/220; 514/456, 455, 100

(56) References Cited

U.S. PATENT DOCUMENTS

| | | | |
|---|---|---|---|
| 3,867,541 A | 2/1975 | Robbins | 424/283 |
| 6,500,846 B1 | 12/2002 | Hong et al. | 514/321 |
| 6,506,792 B1 | 1/2003 | Reed et al. | 514/456 |

OTHER PUBLICATIONS

Varma et al 'Solventless regeneration of ketones from thioketones using clay supported nitrate salts and microwave irradiation' CA 130:311380 (1999).*

Levai et al 'An efficient procedure fro the preparation f 4–thioflavones by the reaction o fflavones with Lawesson's reagent' CA 132:122483 91999.*

Elisei et al 'Photophysical properties of hydroxy–substituted flavothiones' CA 133;119982 (2000).*

Homma et al 'Discovery of biologically active compounds from human adminstered Kampo–medicine XVI. Pharmacological activities of urinary products of saibokuto' CA 124:332246 91996.*

Namgoong et al 'Effects ofnaturally occurring flavonoids on mitogen–induced lymphocyte proliferation and mixed lymphocyte culture' 120;152983 (1994).*

Cushman et al 'Synthesis and protein–tyrosine kinase inhibitory activities of flavonoid analogs' CA 114: 163804 (1991).*

Hirano et al 'Effects of synthetic and naturally occurring falvonoids on mitogen–induced proliferation of human peripheral–blood lymphocytes' CA 11:224821.*

\* cited by examiner

*Primary Examiner*—Amelia Owens
(74) *Attorney, Agent, or Firm*—Robert D. Buyan; Stout, Uxa, Buyan & Mullins, LLP

(57) ABSTRACT

3-Deoxyflavonoid compounds and methods for inhibiting T-cell activity and treating diseases and disorders (e.g., autoimmune disorders, inflammatory disorders, diabetes, ALS, MS, rheumatoid arthritis, etc.). In some cases the efficacy and/or duration of action of luteolin and/or other 3-dioxyflavinoid compounds may be increased by administering such compounds along with Rutin, a Rutin congener and/or a Rutin derivative. Also, in some cases, first pass metabolism of luteolin or other 3-deoxyflavinoids may be avoided by administering such compounds by parenteral routes (e.g., sublingual, buccal, intranasal, injection, etc.).

110 Claims, 7 Drawing Sheets

…

Figure 1:
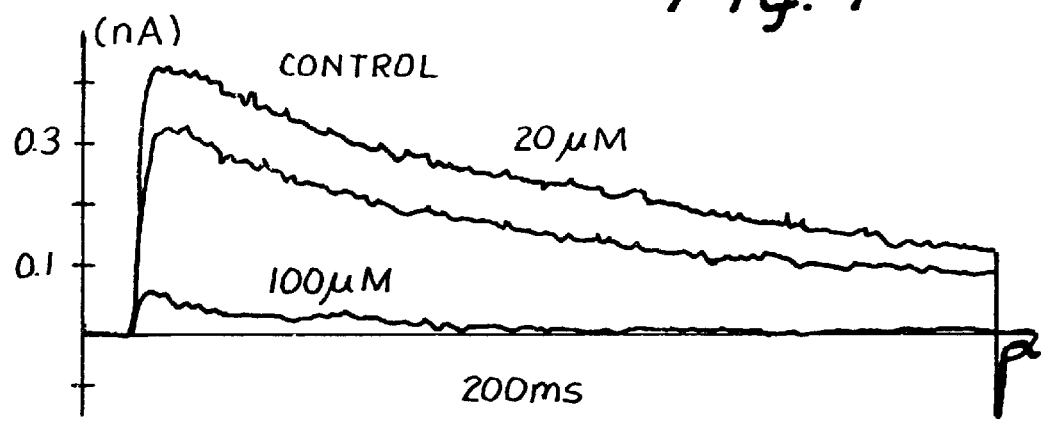

INHIBITION BY 3-DEOXYFLAVONOIDS OF T-LYMPHOCYTE ACTIVATION AND THERAPIES RELATED THERETO

RELATED APPLICATIONS

This application claims priority to United States Provisional Application No. 60/317,666, filed Sep. 6, 2001 and the United States Provisional Application entitled "Parenteral Administration of 3-Deoxyflavinoids to Avoid First Pass Metabolism filed on Aug. 30, 2002 U.S. Ser. No. 60/407,125 the entire contents of which are hereby incorporated by reference

FIELD OF THE INVENTION

This invention relates generally to chemical compositions, preparations and methods for medical treatment and more particularly to the use of certain substituted 3-Deoxyflavonoid compounds for immunosuppressive treatment of autoimmune disorders or inflammatory diseases in mammalian patients.

BACKGROUND OF THE INVENTION

Flavonoids are polyphenolic compounds that occur ubiquitously in foods of plant origin. Over 4000 structurally unique flavonoids have been identified in plant sources (Harborne et al., 1975 The Flavonoids, Academic Press, New York; Cody V, Middleton E, Harborne J B and Beretz A eds; Alan R. Liss, Inc, New York, 1986 Plant Flavonoids in Biology and Medicine, Part 1 and 2). The flavonoids are found in fruits, vegetables, nuts, seeds, herbs, spices, stems, flowers, as well as tea and red wine and are prominent components of citrus fruits and other food sources and are consumed regularly with the human diet.

Flavonols, which are not claimed in this invention, are the most abundant naturally occurring flavonoids and their content in the most common edible fruits, vegetables, and seeds may reach up to a few hundred mg $kg^{-1}$ of fresh weight. Early estimations showed the daily average intake of total flavonoids to be about 1.0 g, with 115 mg being the share of flavonols and flavones. Recently, the "Seven Countries Study" revealed that total daily flavonoid intake may vary from 2.6 to 68.2 mg, with the percentage of quercetin being 39–100%. In another study on 17 volunteers from 14 countries, mean consumption of quercetin and kaempferol was found to be approximately 28 mg/day (Makris and Rossiter, 2001 J. Agric. Food Chem., 49, 3216).

The investigations on the effects of flavonoid-containing plant foods have been based, to a great extent, on the basis of analytical data from raw plant tissues, and thus they actually represent the composition of foodstuffs only in their raw state. Environmental variables and processing may affect to a significant extent the concentrations and biological activities of flavonoids, and these factors have not been taken into consideration. The very few recent research studies on the impact of common domestic and industrial processing practices on flavonoid composition of plant foods show that common domestic processes such as boiling, frying, and microwave cooking can lower quercetin concentrations in onions and tomatoes by 35–82%. Moreover, blanching has been found to reduce quercetin and kaempferol levels in onions by 39 and 64%, respectively, and myricetin and quercetin in sweet potato leaves by 19 and 50%, respectively. This aspect, nevertheless, is of great importance, considering that only a small amount of fruits and vegetables are consumed in their raw state, whereas most of them need to be processed for safety, quality, and economic reasons.

An estimation of the total flavonoid intake is difficult, because only limited data on contents of foods are available. There have been several efforts to quantitate the amounts of different flavonoids in assorted food plants. According to Hertog et al. (1992) J Agric Food Chem 40: 2379–2383, the mean daily intake of mixed flavonoids was only 23 mg/day based on data from the 1987–88 Dutch National Food Consumption Survey. The measured flavonoids were the 3-hydroxy flavones, quercetin, kaempferol, myricetin, and the 3-deoxyflavones, apigenin, and luteolin. The intake of these five antioxidant flavonoids was 23 mg/day, which exceeds the intake of other familiar antioxidants such as β-carotene (2–3 mg/day) and vitamin E (7–10 mg/day) and is about one-third the average intake of vitamin C (70–100 mg/day). The amount of 23 mg/day was mostly flavonols and flavones measured as aglycones and the flavonoid consumed most (16 mg/day) was quercetin. However, it should be stressed that recent evidence indicates that flavonoid-glycosides are much more readily absorbed (than the aglycones) by humans (Hollman and Katan, 1998 Arch Toxicol Suppl 20: 237–248 and Absorption, metabolism, and bioavailability of flavonoids, in Flavonoids in Health and Disease (Rice-Evans C A and Packer L eds, 1998 pp 483–522, Marcel Dekker, Inc., New York.). Moreover, both the amount and the source vary appreciably in different countries and with the exception of the Mediterranean diet, which is rich in olive oil, citrus fruits, and greens, it is very likely that most developed countries lack diets rich in the flavonoids, and particularly, 3-deoxyflavonoids, which could provide pharmacologically significant concentrations in body fluids and tissues.

The flavonoids are typical phenolic compounds and, therefore, act as potent metal chelators and free radical scavengers and are powerful chain-breaking antioxidants. They have beneficial health effects partly because of these antioxidant properties. The flavonoids display a remarkable array of biochemical and pharmacological actions, some of which suggest that certain members of this group of compounds may significantly affect the function of various mammalian cellular systems. They have long been recognized to possess anti-inflammatory, antioxidant, antiallergic, hepatoprotective, antithrombotic, antiviral, and anticarcinogenic activities. However, Rimm and coworkers (1996 Ann Intern Med 125: 384–389) did not find a strong inverse association between intake of flavonoids and total coronary heart disease. The intake of flavonols and flavones was inversely associated with subsequent coronary heart disease in most but not all prospective epidemiological studies.

Vegetables and fruits often associated with low rates of cancer in epidemiological studies are not major sources of dietary flavonols and flavones and therefore these may not be directly responsible to the cancer-protective effect; a protective effect against cardiovascular disease is also not conclusive. Furthermore, It has also been established in the literature that quercetin, a flavonol (3-hydroxyflavone), has mutagenic properties and therefore its glycoside, rutin, is expected to behave similarly due to its facile hydrolysis to quercetin. The inventors have unexpectedly found that flavonols may have an adverse effect to that exerted by 3-deoxyflavonoids of this invention and may counteract the therapeutic benefits of the latter.

Flavonoids present in foods were considered non-absorbable because they are bound to sugars as β-glycosides. However, it is known that human absorption of the quercetin glycosides from onions (52%) is far better than that of the pure aglycone (24%) as shown by researchers in the Netherlands. Using more recent analytical techniques, plasma quercetin concentrations were measured following ingestion of fried onions containing quercetin glycosides equivalent to 64 mg of quercetin aglycone (Hollman et al., 1996 *Free Radical Biol Med* 21: 703–707). Peak plasma levels of 196 µg/ml were achieved after 2.9 h with a half-life of absorption of 0.87 h. The distribution phase half-life was 3.8 h and the elimination phase half-life was 16.8 h. Thus, oral dietary (cooked vegetable) quercetin can be absorbed and reach tissues and plasma where antioxidant and other activities could be exerted. What is true for quercetin is very likely true also for other flavonoids in other vegetable sources. Hollman and Katan (1998 *Arch Toxicol Suppl* 20: 237–248) reviewed the bioavailability and health effects of dietary flavonols in humans. They found that quercetin glycosides from onions were more readily absorbed than the pure aglycone; absorbed quercetin was eliminated slowly from the blood, suggesting once again that the enterohepatic circulation may be operative. In related studies, Hollman et al. (1995 *FEBS Lett* 418: 152–156) concluded that quercetin-glucose conjugates were more readily absorbable; the suggestion was made that the glycosides may be absorbed via the intestinal sugar uptake route. It is apparent from the prior art that the ingested flavonoid glycosides are rapidly metabolized to aglycones by ubiquitous glycosidases and the pharmacokinetic parameters change dramatically due to poor solubility of the aglycones. The oral absorption and bioavailability of aglycones become a critical issue for treatment of therapeutic disorders. The formulations described in this invention utilize absorption enhancers, which also act as solubilizing agents, and are expected to facilitate the absorption of the aglycone to overcome this problem. Moreover, many of the 3-deoxyflavonoids of Formula I of this invention have been designed to increase their water solubility significantly over the corresponding aglycones and these are anticipated to show much improved pharmacokinetic profiles.

The complex nature of botanicals or herbals present some special challenges. Botanicals typically consist of multiple components, some of which may be active individually or in combination with each other. Such multiple active entities may exhibit agonist or antagonist activity, although having a common structural backbone. Identifying the bioactive components is absolutely critical to resolve the question of bioavailability and to establish meaningful standards for dissolution, bioavailability, potency content, uniformity and stability.

The complex activity-composition relationship of botanicals presents a unique challenge to understanding the effect of formulation and process variables on product quality and establishing good manufacturing practices to assure that the appropriate quality and performance standards are being met (Augsburger, 2001 in Examining the Science behind Nutraceuticals, AAPS Press). Environmental variables and processing may affect to a significant extent the concentration and biological activity.

One of the alternate approaches to this problem is to identify and synthesize the active principle in its purest form to avoid the unwanted components that may have undesired or no biological activities.

These low molecular weight substances, found in all vascular plants, are phenylbenzo-pyrones (phenylchromones) with an assortment of structures based on a common three-ring nucleus. They are usually subdivided according to their substituents into flavanols, anthocyanidins, flavones, flavanones, and chalcones. The basic flavone and flavanone structure is comprised of two benzene rings (A and B) linked through a heterocyclic pyrone ring in the middle (Formula I). The 3-deoxyflavonoid compounds of this invention are particularly based on the presence (or absence) of a double bond between carbon atoms 2 and 3 of the pyran ring, and the absence of hydroxyl group in the 3-position of the middle pyrone ring (Formula I). In the flavonoid structure, a phenyl group is usually substituted at the 2-position of the pyrone ring. In isoflavonoids, the substitution is at the 3-position and genistein and daidzein are included in the composition of this invention.

Diabetes and autoimmune disorders together affect nearly 10% of the global population. Autoimmune diseases involve aberrant regulation of cellular and humoral mediated immunity and are frequently associated with abnormal or enhanced T cell, B cell and macrophage effector functions directed towards self antigens. The activation of these cellular components towards self antigens is believed related to the break in feedback mechanisms associated with self tolerance. Autoimmune diseases encompass a whole spectrum of clinical entities and despite the differences in the target organ have many similarities (Ahmed et al., Am J. Path., 121:531 (1985)). In addition, these diseases are all characterized by their chronicity, the tendency of clinical remission and "flare ups" for poorly understood reasons, and the involvement of other organs. While the presence of autoantibodies, inappropriate expression of class II antigens, macrophage activation and T cell infiltration to the target organ have been described in essentially all of the autoimmune diseases, neither the triggering mechanisms which result in disease activation nor disease progression are well understood. Accordingly, therapy for these diseases is largely unsatisfactory and involves the use of gold salts, methotrexate, antimalarials, glucocorticoids (methylprednisolone), beta interferon, and other immunosuppressives as well as plasmapheresis and attempts at inducing tolerance. Treatment of autoimmune diseases has not improved significantly over the past decade and primarily is associated with the use of nonsteroidal and steroidal anti-inflammatory agents to treat the symptoms of the disease. Clearly while suppression of the specific immune response directed against the host is necessary, generalized immunosuppression as with glucocorticoids has major liabilities in terms of side effect profile and the propensity of the immunosuppressed patient to be at greater risk for other infectious and non-infectious diseases.

Estrogen appears to be involved with autoimmune diseases although its role in disease progression or regression is complex and dependent on the nature of the autoimmune disease. Estrogen for example appears to have an ameliorating effect on rheumatoid arthritis while having an exacerbating effect on systemic lupus (Chander & Spector; Ann. Rheum. Dis. 50:139). Estrogen has been demonstrated to have a suppressive role on T cell function and yet an immunostimulatory effect on B cells. Therefore, estrogen-like compounds should prove beneficial in diseases associated with activated T cells including rheumatoid arthritis, multiple sclerosis, Guillan Barre syndrome and Hashimoto's thyroiditis through inhibition of T cell function (Holmadahl, J. Autoimmun. 2:651 (1989).

Glucocorticoids and other immunosuppressive medications, for example cyclophosphamide (CPA), are of crucial importance for the survival of patients with systemic lupus erythematosus. There is as yet no specific curative agent. To date, therapy has been aimed at preventing or overcoming acute exacerbation and averting recurrences.

For this purpose, the patients have been treated with glucocorticoids and other immunosuppressants, but these themselves have hazardous side effects.

Angiogenesis-dependent diseases (i.e., those diseases which require or induce vascular growth) represent a significant portion of all diseases for which medical treatment is sought. For example, cancer is the second leading cause of death in the U.S., and accounts for over one-fifth of the total mortality. Briefly, cancer is characterized by the uncontrolled division of a population of cells which, most typically, leads to the formation of one or more tumors. Such tumors are also characterized by the ingrowth of vasculature which provide various factors that permit continued tumor growth. Although cancer is generally more readily diagnosed than in the past, many forms, even if detected early, are still incurable.

A variety of methods are presently utilized to treat cancer, including for example, various surgical procedures. If treated with surgery alone however, many patients (particularly those with certain types of cancer, such as breast, brain, colon and hepatic cancer) will experience recurrence of the cancer. Therefore, in addition to surgery, many cancers are also treated with a combination of therapies involving cytotoxic chemotherapeutic drugs (e.g., vincristine, vinblastine, cisplatin, methotrexate, 5-FU, etc.) and/or radiation therapy. One difficulty with this approach, however, is that radiotherapeutic and chemotherapeutic agents are toxic to normal tissues, and often create life-threatening side effects. In addition, these approaches often have extremely high failure/remission rates.

Neovascularization, or angiogenesis, is the growth and development of new arteries. It is critical to the normal development of the vascular system, including injury-repair. There are, however, conditions characterized by abnormal neovascularization, including diabetic retinopathy, neovascular glaucoma, rheumatiod arthritis, psoriasis and certain cancers. For example, diabetic retinopathy is a leading cause of blindness. There are two types of diabetic retinopathy, simple and proliferative. Proliferative retinopathy is characterized by neovascularization and scarring. About one-half of those patients with proliferative retinopathy progress to blindness within about five years. It would be desirable to identify antiangiogenesis agents useful in treating the foregoing diseases. The present invention provides compositions and methods suitable for treatment of cancers, as well as other non-tumorigenic angiogenesis-dependent diseases, and further provides other related advantages.

Autoimmune diseases encompass a whole spectrum of clinical disorders wherein a patient's immune system mistakenly attacks self, targeting the cells, tissues, and organs of the patient's own body. The following are some examples of autoimmune diseases, categorized with respect to the target organ that is principally affected by each such disease:

| Nervous System: | Gastrointestinal Tract: |
| --- | --- |
| Multiple sclerosis | Crohn's Disease |
| Myasthenia gravis | Ulcerative colitis |
| Autoimmune neuropathies such as Guillain-Barré | Primary biliary cirrhosis Autoimmune hepatitis |
| Autoimmune uveitis | Endocrine: |
| Blood: | Type 1 diabetes mellitus |
| Autoimmune hemolytic anemia | Addison's Disease |

| -continued | |
| --- | --- |
| Pernicious anemia | Grave's Disease |
| Autoimmune thrombocytopenia | Hashimoto's thyroiditis |
| Vascular: | Autoimmune oophoritis and |
| Temporal arteritis | orchitis |
| Anti-phospholipid syndrome | Multiple Organs and/or |
| Vasculitides such as | Musculoskeletal System: |
| Wegener's granulomatosis | Rheumatoid arthritis |
| Behcet's disease | Systemic lupus erythematosus |
| Skin: | Scleroderma |
| Psoriasis | Polymyositis, dermatomyositis |
| Dermatitis herpetiformis | Spondyloarthropathies such as |
| Pemphigus vulgaris | ankylosing spondylitis |
| Vitiligo | Sjogren's syndrome |
| | Interstitial Cystitis |

Irrespective of the particular organ(s) affected, T-lymphocytes are believed to contribute to the development of autoimmune diseases. The currently available therapies for these diseases are largely unsatisfactory and typically involve the use of glucocorticoids (e.g. methylprednisolone, prednisone), non-steroidal anti-inflammatory agents, gold salts, methotrexate, antimalarials, and other immunosuppressants such as cyclosporin and FK-506. Unfortunately, these T-cell inhibiting drugs are toxic, with liver and renal toxicities limiting their use.

Thus, the search for additional immunosuppressive agents for the treatment of autoimmune and inflammatory disorders occupies considerable attention in the pharmaceutical industry. Since cytokines such as interferon-gamma and tumor necrosis factor-alpha play a critical role in the pathophysiology of autoimmune disorders, much effort has been invested in the development of agents that suppress their production, secretion and/or end-organ effect.

There is an excellent track record of treating nervous and cardiovascular disorders with ion channel modulators—either openers or blockers. Ion channel blockers as a general class, represent the major therapeutic agents for treatment of stroke, epilepsy and arrhythmias. Since ion channels play a major role in the T-cell immune response, these channels may represent attractive targets for pharmaceutical immunomodulation.

Potassium ($K^+$) channels are found in all tissues of the body and play a multiplicity of roles ranging from homeostatic regulation of cell volume and osmotic balance, to modulating electrical signaling in nerve and muscle cells, to regulating the secretion of transmitters at nerve terminals and hormones in endocrine cells. To mediate these diverse functions, there are about 80 genes that encode $K^+$ channels. Among all ion channels, the $K^+$ channel superfamily is by far the most diverse. The $K_{ATP}$ channel is an important target for antidiabetic agents that promote insulin release (Potassium Channels: Molecular Defects, Diseases, and Therapeutic Opportunities, Shieh C—C et al, 2000 Pharmacol Rev, 52, 557–583 and references cited therein).

$Ca^{++}$ mediated signaling events are central to the physiological activity of diverse cell types. Opening in response to changes in intracellular $Ca^{++}$ ($[Ca^{++}]_i$), $Ca^{++}$-activated $K^+$ ($K_{Ca}$) channels play an important role in modulating the $Ca^{++}$ signaling cascade by regulating the membrane potential in both excitable and non-excitable cells. Historically, these channels have been classified as large-($BK_{Ca}$), intermediate-($IK_{Ca}$) and small-($SK_{Ca}$) conductance channels based on their single-channel conductance (100–250 pS, 11–40 pS and 4–14 pS respectively) in symmetrical $K^+$ solutions. $BK_{Ca}$ channels, abundant in smooth muscle and in neurons, but also present in other cells, are opened by elevated $[Ca^{++}]_i$ as well as depolarization, and are blocked by the scorpion peptides charybdotoxin (ChTX) and iberiotoxin.

$SK_{Ca}$ channels are highly sensitive to $[Ca^{++}]_i$, with activation in the 200–500 nM range, and are voltage-independent. $SK_{Ca}$ channels are highly expressed in the central nervous system, in skeletal muscle and in human Jurkat T-cells and are blocked by apamin, a peptide from bee venom, and by the scorpion peptide, scyliatoxin. Three genes (SKCa1–3) within a novel sub-family encode $SK_{Ca}$ channels.

$IK_{Ca}$ channels, unlike $SK_{Ca}$ channels, are predominantly expressed in peripheral tissues including those of the hematopoietic system, colon, lung, placenta and pancreas. These channels can be pharmacologically distinguished from $SK_{Ca}$ channels by their sensitivity to block by ChTX and clotrimazole, and by their insensitivity to apamin. Both $SK_{Ca}$ and $IK_{Ca}$ channels are voltage-independent and steeply sensitive to a rise in $[Ca^{++}]_i$. At least one gene, called IKCa1, has been shown to encode the native $IK_{Ca}$ channel in human T-lymphocytes and erythrocytes and colonic epithelium. Human IKCa1 shares only about 40% identity with the SKCa1–3 gene products and comprises a distinct sub-family within the extended $K^+$ channel super-gene family.

In pancreatic beta cells, insulin secretion is triggered by a rise in blood glucose coupled metabolically to the closing of $K_{ATP}$ channels. When $K_{ATP}$ channels close, the membrane potential depolarizes, resulting in activation of voltage-gated $Ca^{2+}$ channels and regulated exocytosis of granules containing insulin. Sulfonylurea compounds such as glimepiride are used to treat Type-II diabetes to enhance insulin release from islets. These drugs work by blocking $K_{ATP}$ channels. Islets also express the Kv1.7 channel, and increased Kv1.7 mRNA levels are detected in the islets of diabetic db/db rats (Kalman et al., 1998 J. Biol. Chem. 273: 5851). Recent studies have also identified a variety of KCa channels in islets, and SKCa3 has been shown to modulate insulin secretion under some circumstances in transgenic mice (Tamarina et al., 2001 Biophysical Society Abstract 1472). Calcium channels in these cells also are required for insulin secretion. The 3-deoxyflavonoid compounds might modulate blood sugar by targeting one or more of these channels.

The predominant voltage-gated channel in human T-lymphocytes is encoded by Kv1.3, a Shaker-related gene. Kv1.3 has been characterized extensively at the molecular and physiological level and plays a vital role in controlling T-lymphocyte proliferation, mainly by maintaining the resting membrane potential of resting T-lymphocytes. Highly specific peptide blockers of this channel such as Margatoxin and ShK-Dap[22] (Kalman 1998, J. Biol. Chem. 273: 32697), inhibit the ability of quiescent T-lymphocytes to undergo mitogen-induced activation. Human T-lymphocyte activation is accompanied by a ~2-fold increase in Kv1.3 currents, while $K_{Ca}$ currents are up-regulated 10–25-fold (Zweifach 1993, Proc. Natl. Acad. Sci. USA 90: 6295 and Chandy 1993, Seminars in The Neurosciences 5: 125).

The early stages of T-cell activation may be conceptually separated into pre-$Ca^{++}$ and post-$Ca^{++}$ events. Following engagement of antigen with the T-cell antigen-receptor, activation of tyrosine kinases and the generation of inositol 1,4,5-triphosphate leads to the influx of $Ca^{++}$ through Calcium-Release Activated Calcium (CRAC) channels and the rise of cytoplasmic $Ca^{++}$ concentration (Kerschbaum and Cahalan 1999 Science 283: 836 and references cited therein). The rise in $Ca^{++}$ activates the phosphatase calcineurin, which then dephosphorylates a cytoplasmically localized nuclear factor of activated T cells (NF-AT) enabling it to accumulate in the nucleus and bind to a promoter element of the interleukin-2 gene. Along with parallel events involving the activation of protein kinase C and ras, gene transcription leads to lymphokine secretion and to lymphocyte proliferation. Some genes require long-lasting $Ca^{++}$ signals while others require only a transient rise of $Ca^{++}$. Furthermore, $Ca^{++}$ immobilization of the T-cell at the site of antigen presentation helps to cement the interaction between T-cell and the antigen-presenting cell and thereby facilitate local signaling between the cells. Production of the key T cell cytokine IL-2 requires the simultaneous activation of both pathways, with $Ca^{2+}$ being absolutely required for the process.

Two distinct types of potassium channels (the voltage-gated Kv1.3 channel and the intermediate-conductance calcium-activated potassium channel, IKCa1) indirectly determine the driving force of calcium entry through the store-operated $Ca^{++}$ channel. When these potassium channels open, the resulting efflux of $K^+$ hyperpolarizes the membrane, which in turn accentuates the entry of $Ca^{++}$, which is absolutely required for downstream activation events (Cahalan and Chandy 1997, Curr. Opin. Biotechnol. 8: 749). Blockers of the Kv1.3 and IKCa1 channels suppress human T-cell activation, when applied independently, and produce greater suppression when applied together. One mechanism for the immunosuppression by $K^+$ channel blockers is via membrane depolarization, which reduces $Ca^{++}$ entry through CRAC channels in the T-cell membrane, which in turn leads to suppression of calcium-dependent signaling events during human T-cell activation. Together with their predominant expression in peripheral tissue, the upregulation in the wake of T-lymphocyte activation makes IKCa1 channels an extremely attractive target for the development of novel immunosuppressive agents. The most specific available inhibitor of IKCa1, the azole antimycotic clotrimazole, has recently been shown to potently inhibit T-lymphocyte proliferation (Khanna 1999, J. Biol. Chem. 274: 1483822). However, clotrimazole is also a potent inhibitor of many mammalian cytochrome P-450-mediated reactions and is not an ideal therapeutic candidate. 1-[(2-chlorophenyl)diphenylmethyl]-1H-pyrazole, a triaryl methane analog of clotrimazole, has been shown to inhibit the cloned and the native IKCa1 channel in human T-lymphocytes with a $K_d$ of 20–25 nM, and is 200–1500 fold selective over other ion channels (Wulff 2000, Proc. Natl. Acad. Sci. USA 97: 8151).

Given the shortcomings associated with the currently available modes of therapy for autoimmune disorders there remains a need for the development of new immunosuppressive drugs that are capable of selectively inhibiting the activation of T-lymphocytes with minimal side effects.

SUMMARY OF THE INVENTION

In accordance with the present invention, there are provided methods for inhibiting the activation or proliferation of T-lymphocytes in human or veterinary patients by administering to the patient a T-lymphocyte-inhibiting amount of a compound of general formula I, as follows:

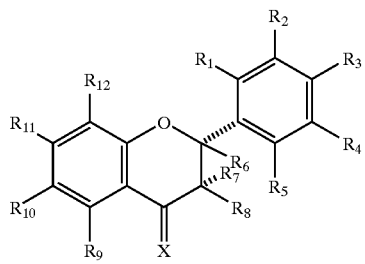

Wherein,

X is selected from O and S;

$R_1$ through $R_5$ and $R_9$ through $R_{12}$ are selected from H, OH, Halogen such as F or Cl, Alkyl, Amino, NHMe, SH, Sme, Cyano, Carboxyl, Carboxyalkyl, Carboxamide, alkoxycarbonyl, O-Hydroxyalkyl, $CF_3$, O-Alkyl, O—$SO_3H$, O—$SO_2H$, O—$PO_3H$, O-Glycoside, O-Glucoronide and O-Amino Acid, including O—CO—A—$(CH_2)_n$—NR'R", where A is Phenyl, substituted phenyl or absent; n is 0 through 5; R' and R" are selected from H, lower alkyl, hydroxyalkyl, aminoalkyl, mono and dialkylaminoalkyl, carboxyalkyl or R' and R" may combine to form a cyclic ring, optionally substituted with a O, S, NH or N-Alkyl and the methylene adjacent to the nitrogen may be optionally substituted with a amino alkyl, carboxy or carboxyalkyl group and O—CO—NH—$(CH_2)$m—CH—$(NH_2)$COOH, where m is 1 through 4;

$R_6$ and $R_7$ are H or may combine to form a doublebond;

$R_8$ is selected from H, Halogen such as F or Cl, Alkyl, Amino, Cyano, Carboxyl, Carboxyalkyl, Carboxamide, alkoxycarbonyl and $CF_3$. Furthermore, when $R_1$ through $R_5$ and $R_9$ through $R_{12}$ are OH and are present on adjacent ring carbons then they may be combined through a methylene (—O—CH2—O—) or a carbonyl (—O—CO—O—) group to form a cyclic ring. Most preferred are 6,7 and 7,8-methylenedeoxy and 3',4'-carbonyloxy (cyclic carbonate) derivatives.

Such method may be carried out for the purpose of treating any disease or disorder characterized by excessive or aberrant activity of T-lymphocytes. Such diseases and disorders include but are not necessarily limited to autoimmune disorders, diabetes, amilotropic lateral sclerosis (ALS), rheumatoid arthritis, systemic lupus erythmatosis (SLE), graft-host disease, graft rejection, Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Graves' Disease, Guillain-Barré, Hashimoto's Thyroiditis, Idiopathic Pulmonary Fibrosis, Idiopathic Thrombocytopenia Purpura (ITP), IgA Nephropathy, Insulin dependent Diabetes, Juvenile Arthritis, Lichen Planus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agamma-globulinemia, Primary Biliary Cirrhosis, Psoriasis, Raynaud's Phenomenon, Reiter's Syndrome, Rheumatic Fever, Sarcoidosis, Scieroderma, Sjögren's Syndrome (primary or secondary), Stiff-Man Syndrome, Takayasu Arteritis, Temporal Arteritis/Giant Cell Arteritis, Ulcerative Colitis, Uveitis, Vasculitis, Vitiligo, Wegener's Granulomatosis, etc. as well as the various inflammatory and other diseases and disorders stated in the detailed description of the invention set forth herebelow.

Still further in accordance with the invention, when the foregoing method is carried out for the purpose of treating diabetes or stabilizing the patient's blood glucose levels, the compound may comprise any compound of General Formula I except for luteolin (i.e., the 3',4',5,7-tetrahydroxyflavone compound of General Formula I wherein X=O and wherein $R_2,R_3,R_9,R_{11}$=OH), the 5 glucoside of luteolin, the 7 glucoside of luteolin, or apigenin.

Still further in accordance with the invention, when the foregoing method is carried out for the purpose of treating or preventing Amylotropic Lateral Sclerosis (ALS), the method may comprise administering one or more compounds of General Formula I except for luteolin alone, genistein alone, or daidzein alone or the possible combinations of two or more compounds selected from the group of luteolin, genistein and daidzein.

Still further in accordance with the invention, there are provided methods for inhibiting ion flux through certain intracellular ion channels, such as the Kv1.3 channel, by administering effective amounts of the compounds of General Formula I above. Included among these compounds are, for instance, substituted 3-Deoxyflavonoids. These compounds of General Formula I may be administered in combination with other agents such as other IKCa1 blockers such as clotrimazole, 1-[(2-chlorophenyl)diphenylmethyl]-1H-pyrazole, 2-chlorophenyl diphenyl cyanomethane or cyclosporin A or TNF-α inhibitors or other T-lymphocyte inhibitors such as leflunomide, its metabolite A-771726 [N-(4-trifluoromethylphenyl)-1-cyano-2-ketopropyl-carboxamide] or N-[4-(trifluoromethyl)phenyl]-2-hydroxy-6-oxocyclopentanecarboxamideorN-[4-(trifluoromethyl)phenyl]-2-hydroxybenzamide and methods for immunosuppressive treatment of autoimmune disorders by administering therapeutically effective amounts of such compounds to mammalian patients. Through inhibition of the Kv1.3 channel the compounds of General Formula I can lower and stabilize blood glucose levels in Type-I and Type-II diabetics, and can also ameliorate symptoms of lupus erythematosus, an autoimmune disease affecting several organs. Type-I diabetes is, at least in some patients, an autoimmune disease in which autoreactive lymphocytes destroy pancreatic p-cells, while the etiology of Type-II diabetes is due to inadequate insulin production and decreased ability of insulin to affect its target end-organs. Since ion channels play a critical role in lymphocytes and in pancreatic β-cell signaling, it is most likely that at least some of the therapeutic effects of flavonoids may arise through blockade of ion channels. Using patch-clamp experiments, applicant has discovered that Kv1.3, a voltage-gated $K^+$ channel that regulates mitogenesis in human T lymphocytes, can be blocked by the compounds of General Formula I above. The non-toxic nature of these flavonoids in humans makes them attractive as nutraceuticals that could complement or replace existing medications and therapies.

Still further in accordance with the invention, the foregoing method may comprise administering a compound according to General Formula I in combination with elemental Vanadium or Vanadium-containing compound(s). Vanadium compounds are being investigated clinically for their insulin-mimetic effects. Micromolar concentrations of vanadate and peroxovanadium compounds stimulate hexose uptake, glucose oxidation, and lipogenesis in vivo and in vitro. Clinical trials demonstrating that sodium metavanadate and vanadyl sulfate improve insulin sensitivity and fasting blood glucose levels have led to suggestions for use of these agents in adjunctive therapy in diabetes. It is likely that a combination of vanadium compounds and the 3-deoxyflavonoids may interact with lymphocytes and islet cells in an additive or perhaps a synergistic fashion and may have relevance to their proposed clinical application and yield new approaches to the management of diabetes and autoimmune disorders.

Still further in accordance with the present invention, certain compounds of General Formula I, such as luteolin, are known to undergo first pass metabolism when administered orally and absorbed via the gastrointestinal mucosa. Therefore, such compounds may be administered by a parenteral route (i.e., a route by which the compound is substantially absorbed through other than the gastric and/or intestinal mucosa) such as sublingual, buccal, intranasal, transdermal, etc. Such parenteral administration of these compounds can increase the circulating blood levels of the compounds and/or delay the metabolism of the compounds so as to thereby increase their efficacy.

Still further in accordance with the present invention, the efficacy and/or duration of action of luteolin and at least some of the other compounds of General Formula I may be enhanced by administering Rutin or a congener or derivative of Rutin in combination with such compound(s) of General Formula I. This potentiating effect of Rutin and/or congeners or derivatives of Rutin may be due to inhibition of one or more liver enzymes (e.g., certain cytochrome P450 enzymes) thereby slowing the metabolic inactivation of the luteolin or other compound of General Formula I.

Still further in accordance with the present invention, there are provided methods for treating diabetes or stabilizing blood glucose levels by administering an effective amount of a compound of General Formula I other than a) luteolin, the 5 (i.e., $R_9$) glucoside of luteolin the 7(i.e., $R_{11}$) -glucoside of luteolin and apigenin (i.e., the 4',5,7-trihydroxyflavone compound of General Formula I wherein X=O and $R_3,R_9,R_{11}$ are OH).

Still further in accordance with the present invention there is provided a method for treating Amylotrophic Lateral Sclerosis (ALS) in a human or veterinary patient by administering to the patient a therapeutically effective amount of a compound of General Formula I other than luteolin (i.e., the 3',4',5,7-tetrahydroxyflavone compound of General Formula I wherein X=O and wherein $R_2,R_3,R_9,R_{11}$=OH), genistein (i.e., 5,7-Dihydroxy-3-(4-hydroxyphenyl)--4H-1benzopyran-4-one or 4',5,7-trihydroxyisoflavone) or daidzein (7-Hydroxy-3-(4-hydroxyphenyl)-4H-1benzopyran-4-one OR 4',7-dihydroxyisoflavone).

In accordance with the invention, there is provided a method for inhibiting cytokine secretion and/or for treating autoimmune disorders, including diabetes, multiple sclerosis, systemic lupus erythematosus, rheumatoid arthritis and interstitial cystitis, by administering to a mammalian patient a therapeutically effective amount of at least one compound having the general structural Formula I above.

Still further in accordance with the invention, there are provided novel compositions of matter of General Formula II, as follows:

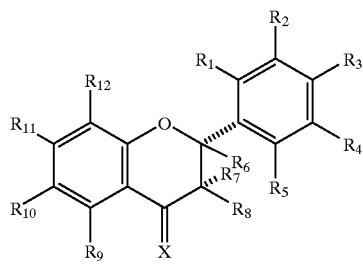

Wherein,
X is selected from O and S; and
i) when X is O,
$R_1$, $R_4$, $R_5$ and $R_8$ are H or F;
$R_6$ and $R_7$ combine to form a double bond;
$R_2$ and $R_3$ are selected from H, OH, SH, Halogen such as F or Cl, Alkyl, Amino, NHMe, Cyano, Carboxyl, Carboxyalkyl, Carboxamide, alkoxycarbonyl, O-Hydroxyalkyl, $CF_3$, O-Alkyl, O—$SO_3H$, O—$SO_2H$, O—$PO_3H$, O-Glycoside, O-Glucoronide and O-Amino Acid, including O—CO—A—$(CH_2)n$—NR'R", where A is Phenyl, substituted phenyl or absent; n is 0 through 5; R' and R" are selected from H, lower alkyl, hydroxyalkyl, aminoalkyl, mono and dialkylaminoalkyl, carboxyalkyl or R' and R" may combine to form a cyclic ring, optionally substituted with a O, S, NH or N-Alkyl and the methylene adjacent to the nitrogen may be optionally substituted with a amino alkyl, carboxy or carboxyalkyl group and O—CO—NH—$(CH_2)m$—CH—$(NH_2)$COOH, where m is 1 through 4; and when $R_2$ and $R_3$ are OH or Amino, they may be optionally combined through a methylene or carbonyl group;
$R_9$ is selected from OH, Amino, NHMe, SH, or SMe; and
$R_{10}$ and $R_{11}$ or $R_{11}$ and $R_{12}$ are methylenedioxy (O—CH2—O), or a cyclic carbonate (O—CO—O), or $R_{12}$ is H and $R_{10}$, $R_{11}$, are selected from H, OH, Halogen such as F or Cl, Alkyl, Amino, Cyano, Carboxyl, Carboxyalkyl, Carboxamide, alkoxycarbonyl, O-Hydroxyalkyl, $CF_3$, O-Alkyl, O—$SO_3H$, O—$SO_2H$, O—$PO_3H$, O-Glycoside, O-Glucoronide and O-Amino Acid, including O—CO—A—$(CH_2)n$—NR'R", where A is Phenyl, substituted phenyl or absent; n is 0 through 5; R' and R" are selected from H, lower alkyl, hydroxyalkyl, aminoalkyl, mono and dialkylaminoalkyl, carboxyalkyl or R' and R" may combine to form a cyclic ring, optionally substituted with a O, S, NH or N-Alkyl and the methylene adjacent to the nitrogen may be optionally substituted with a amino alkyl, carboxy or carboxyalkyl group and O—CO—NH—$(CH_2)m$—CH—$(NH_2)$COOH, where m is 1 through 4; with the proviso that when $R_2$ and/or $R_3$ are H, OH, OMe, Cl, or Amino then $R_9$, $R_{10}$, and $R_{11}$ are not the same.
ii) when X is S,
$R_1$ through $R_5$ and $R_9$ through $R_{12}$ are selected from H, OH, Halogen such as F or Cl, SH, SMe, Alkyl, Amino, NHMe, Cyano, Carboxyl, Carboxyalkyl, Carboxamide, alkoxycarbonyl, O-Hydroxyalkyl, $CF_3$, O-Alkyl, O—$SO_3H$, O—$SO_2H$, O—$PO_3H$, O-Glycoside, O-Glucoronide and O-Amino Acid, including O—CO—A—(CH$_2$)n—NR'R", wherein A is phenyl, substituted phenyl or absent; wherein n is 0 through 5, wherein R' and R" are selected from H, lower alkyl, hydroxyalkyl, aminoalkyl, mono and dialkylaminoalkyl, carboxyalkyl or wherein R' and R" combine to form a cyclic ring, said cyclic ring being optionally substituted with a O, S, NH or N-Alkyl and wherein the methylene adjacent to the nitrogen may be optionally substituted with a amino alkyl, carboxy or carboxyalkyl group and O—CO—NH—(CH$_2$)m—CH—(NH$_2$)COOH wherein m is 1 through 4;

$R_6$ and $R_7$ combine to form a double bond;

$R_8$ is selected from H or F; and, when $R_1$ through $R_5$ and $R_9$ through $R_{12}$ are OH, SH or amino, and are present on adjacent ring carbons then they may be combined through a methylene (—O—CH$_2$—O—) or a carbonyl (—O—CO—O—, O—CO—NH— or —S—CO—NH—) group to form a cyclic ring.

Still further in accordance with the invention, the synthetic reactions and procedures that may be used to prepare compounds of this invention)General Formulas I and II) are known in the prior art and can be applied by any person skilled in the art. As an example, a hydroxy substituted flavone may be treated with a haloacetyl halide and the haloalkyl ester product then treated with an amine to obtain the O-Aminoacyl derivative of interest. Similarly, a catechol derivative can be treated with diethyl carbonate or ethylene carbonate in presence of a base to insert the —O—CO—O— functionality.

DETAILED DESCRIPTION OF THE INVENTION

The following detailed description and examples are provided for the purpose of setting forth examples of the present invention and do not limit the scope of the present invention in any way.

The present invention includes pharmaceutical preparations containing Kv1.3 channel inhibitors, for instance, substituted 3-Deoxyflavonoids compounds as active agents, optionally containing IKCa1 blockers such as clotrimazole, 1-[(2-chlorophenyl)diphenylmethyl]-1H-pyrazole, 2-chlorophenyl diphenyl cyanomethane or cyclosporin A or TNF-α inhibitors or other T-lymphocyte inhibitors such as leflunomide, its metabolite A-771726 [N-(4-trifluoromethylphenyl)-1-cyano-2-ketopropyl-carboxamide] or N-[4-(trifluoromethyl)phenyl]-2-hydroxy-6-oxocyclopentanecarboxamide or N-[4-(trifluoromethyl)phenyl]-2-hydroxybenzamide and methods for immunosuppressive treatment of autoimmune disorders by administering therapeutically effective amounts of such compounds to mammalian patients.

Furthermore, the invention deals with ion channels that constitute a set of molecular targets through which these 3-deoxyflavonoids exert their biological effects. The flavonoid compounds of this invention can lower and stabilize blood glucose levels in Type-I and Type-II diabetics, and can also ameliorate symptoms of lupus erythematosus, an autoimmune disease affecting several organs. Type-I diabetes is an autoimmune disease in which autoreactive lymphocytes destroy pancreatic P-cells, while the etiology of Type-II diabetes is due to inadequate insulin production and decreased ability of insulin to affect its target end-organs. Since ion channels play a critical role in lymphocytes and in pancreatic β-cell signaling, it is most likely that at least some of the therapeutic effects of flavonoids may arise through blockade of ion channels. Using patch-clamp experiments, we have now surprisingly discovered that Kv1.3, a voltage-gated K$^+$ channel that regulates mitogenesis in human T lymphocytes, can be blocked by these 3-deoxy flavonoids (Formula I). The non-toxic nature of these flavonoids in humans makes them attractive as nutraceuticals that could complement or replace existing medications and therapies.

The present invention is directed to a method for suppressing the immune system in a subject in need of such treatment. Specifically, the method of this invention is useful in autoimmune diseases such as rheumatoid arthritis, systemic lupus erythematosis, Hashimoto's thyroiditis, ALS, multiple sclerosis, myasthenia gravis, type I and II diabetes mellitus, nephrotic syndrome, steroid-dependent and steroid-resistant nephrosis, palmar-plantar pustolosis, allergic encephalomyelitis, glomerulonephritis, Behcet's syndrome, ankylosing spondylitis, polymyositis, fibromyositis, etc.

In accordance with the invention, there is provided a method for inhibiting T-lymphocyte activity (and thereby inhibiting cytokine secretion and/or treating autoimmune disorders, including diabetes, ALS, multiple sclerosis, systemic lupus erythematosus, rheumatoid arthritis and interstitial cystitis or any of the other diseases or disorders listed in the Summary of the Invention, above) by administering to a mammalian patient a therapeutically effective amount of at least one compound having the general structural Formula I as shown above. The following compounds of General Formula I are presently preferred for use in the method of the present invention:

6,7 Methylenedioxy-3',4',5-trihydroxyflavone 7,8 Methylenedioxy-3',4',5-trihydroxyflavone 6,7-Carbonyloxy-3+,4',5-trihydroxyflavone 3',4'-Carbonyloxy-5,7-dihydroxyflavone 3',5,7-Trihydroxyflavone-4'-phosphate 3',5,7-Trihdroxy-4'-(2-amino-1-carboxypropyloxy) flavone 5-Hydroxy-3',4',7-tricarboxymethyloxyflavone Additionally, the isoflavonoids, where the phenyl substituent in Formula I occupies the 3-position, are included in the invention. Particularly, the compositions may contain, in addition to one or more 3-deoxyflavonoids, one or more isoflavones and more specifically, genistein (i.e., 5,7-Dihydroxy-3-(4-hydroxyphenyl)-4H-1benzopyran-4-one or 4',5,7-trihydroxyisoflavone) and/or daidzein (i.e., 7-Hydroxy-3-(4-hydroxyphenyl)-4H-1benzopyran-4-one OR 4',7-dihydroxyisoflavone).

When used to treat diabetes, it is preferable that the compounds of the above general formula I are not luteolin (i.e., where $R_2$, $R_3$, $R_9$, $R_{11}$ are OH (3',4',5,7-tetrahydroxyflavone)) or the 5-($R_9$) glucoside of luteolin or the 7-($R_{11}$) glucoside of luteolin or apigenin (i.e., where $R_3$,$R_9$,$R_{11}$ are OH (4',5,7-trihydroxyflavone).

When used to treat Amylotrophic Lateral Sclerosis (ALS), it is preferable that the compounds of the above General Formula I are not luteolin alone, genistein alone, or daidzein alone.

The compounds of this invention are also useful for treating inflammatory, proliferative and hyperproliferative skin diseases and cutaneous manifestations of immunologically mediated illnesses such as psoriasis, psoriatic arthritis, atopic dermatitis, contact dermatitis and other eczematous dermatitises, seborrhoic dermatitis, Lichen planus, Pemphigus, bullous Pemphigus, Epidermolysis bullosa, angiodemas, vasculilides, erythemas, cutanous eosinophilias, acne, Alopecia areata, and arteriosclerosis.

The compounds of the invention are further useful in the treatment of respiratory diseases, for example sarcoidosis, fibroid lung, idiopathic interstitial pneumonia, and reversible obstructive airway diseases, including conditions such as asthma, including bronchial asthma, allergic asthma, intrinsic asthma, extrinsic asthma and dust asthma, bronchitis and the like. The compounds may also be useful for the treating hepatic injury associated with ischemia.

The compounds may also be indicated in certain eye diseases such as keratoconjunctivitis, vernal conjunctivitis, keratitis, uveitis, corneal leukoma, ocular pemphigus, Mooren's ulcer, Scleritis, Graves' ophtalmopathy, sympathetic ophthalmia and the like.

The compounds are also useful treating inflammatory bowel diseases (e.g. Crohn's disease), neurological diseases (including Guillain-Barre syndrome, Meniere's disease, radiculopathy), endocrine diseases (including hyperthyroidism and Basedow's disease), hematological diseases (including pure red cell aplasia, aplastic anemia, hypoplastic anemia, idiopathic thrombocytopenic purpura, autoimmune hemolytic anemia, agranulocytosis and anerythroplasia), bone diseases (including osteoporosis), respiratory disease (including sarcoidosis, idiopathic interstitial pneumonia), skin diseases (including dermatomyositis, leukoderma vulgaris, ichthyosis vulgaris, photoallergic sensitivity and cutanous T cell lymphoma), genitals (orchiitis, vulvitis), circulatory diseases (including arteriosclerosis, polyarteritis nodosa, vasculitis, Buerger's disease, and myocardosis), collagen disorders (including scleroderma, aortitis syndrome, eosinophilic fascitis, Wegener's granulomatosis, Sjogren's syndrome, periodontal diseases), kidney diseases (including nephrotic syndrome, hemolytic-uremic syndrome, Goodpasture's syndrome) and muscular dystrophy. The compounds may also be useful for the treatment of diseases including intestinal inflammations/allergies such as Coeliac disease, proctitis, ulcerative colitis, eosinophilic gastroenteritis, mastocytosis, Crohn's disease and ulcerative colitis and food-related allergic diseases which have symptomatic manifestations remote from the gastrointestinal tract, for example migraine, rhinitis and eczema. Further, the invention can be used for treating preventing or treating inflammation of mucosa or blood vessels (such as leukotriene-mediated diseases), gastric ulcers, vascular damage caused by ischemic diseases and thrombosis, ischemic bowel diseases. Further, the invention will be useful for treating multidrug resistance of tumor cells, (i.e. enhancing the activity and/or sensitivity of chemotherapeutic agents).

The compounds may be useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis, cirrhosis.

Now, it has been shown through anecdotal studies in Type I and Type II diabetic volunteers that the 3-deoxyflavonoids of Formula I lower insulin requirements in diabetics and may have additional beneficial effects on other autoimmune disorders, based upon blockade of ion channels. Results of these ongoing studies have shown dramatic reductions in recalcitrant elevated blood glucose levels and glycosylated hemoglobin (HbAlc), normalization of Type-I blood glucose levels with significantly less insulin, and reduction of other symptoms such as peripheral neuropathy in advanced diabetes, when administered orally as a powder or as a rapidly dissolving tablet. It is believed that the maximum bioabsorption of the 3-deoxyflavonoid takes place through the buccal and sublingual mucosa. Anecdotal studies with volunteers have also suggested efficacy in lupus erythematosus and multiple sclerosis. In addition, we also claim that inhibition of lymphocyte or pancreatic potassium channels may contribute to the diverse biological activities reported for 3-deoxyflavonoids of Formula I, which include spasmolytic, anti-inflammatory, LDL cholesterol lowering, anti-mutagenic and anti-carcinogenic effects. Certain compounds encompassed by Formula I, are safe, naturally occurring flavones and these may be used as neutraceuticals.

It is of paramount interest that by targeting particular channels, or combinations of channels, both primary and secondary immune responses can be inhibited by small molecules without toxicity. Furthermore, it is understood that blockade of Kv1.3 channels, alone or in combination with IKCa1, may provide an even more effective mode of therapy for multiple sclerosis and other autoimmune diseases.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

The following specific examples are set forth in detail to illustrate the invention and should not be considered to limit the invention in any way.

EXAMPLE 1

Inhibition of the Kv1.3 channel was performed utilizing the patch clamp method desctribed by Fanger (2000) J. Biol. Chem. 276: 12249. It was found that luteolin blocked the Kv1.3 channel current approximately 25% at 20 uM concentration and 100% at 100 uM concentration vs. control as shown below in FIG. 1. The results clearly show that luteolin and related 3-deoxyflavonoids are effective in blocking Kv1.3 channels and are therefore effective in treating autoimmune diseases.

EXAMPLE 2

Effect of 3-deoxyflavonoid on the Cytotoxicity of T Lymphocytes

Figure 2:
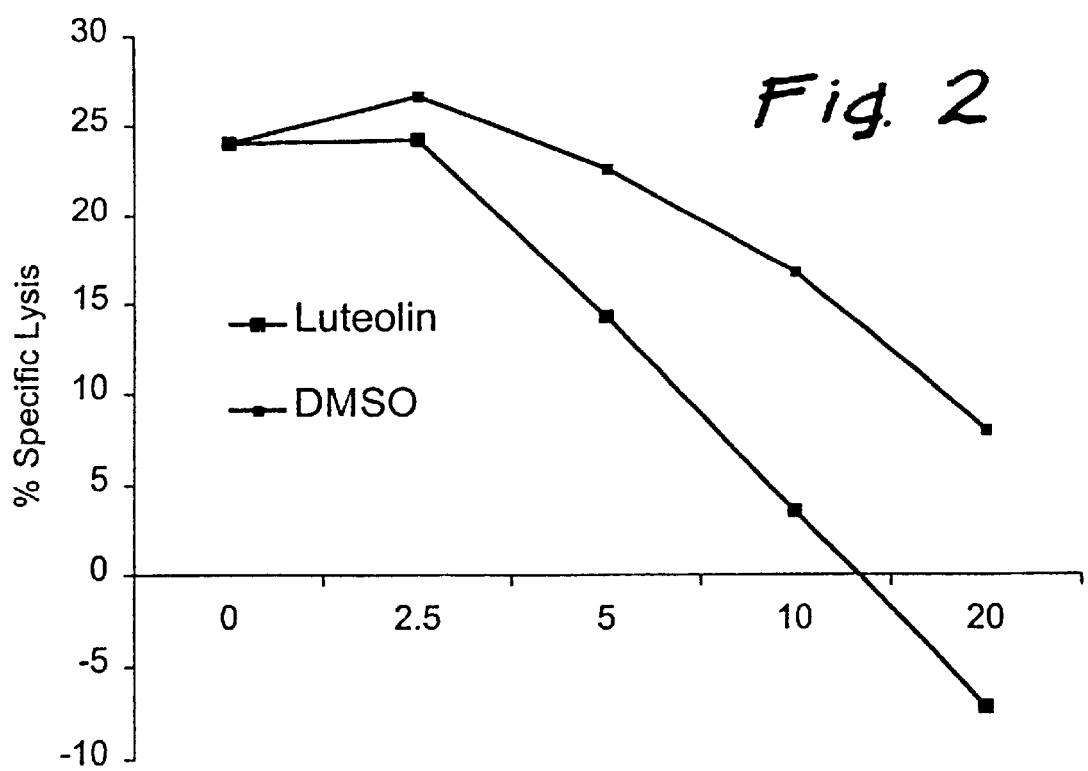

A cytotoxic T lymphocyte line (CTL—designated CTL264) specific for a peptide antigen (aa 264–272, referred to as the 264 peptide) derived from the tumor suppressor protein p53 was used as a target to test if luteolin had any effect on CTL cytotoxicity against 264 peptide-pulsed T2 target cells. T2 target cells were pulsed with 264 peptide for 2 hours and labeled with Calcein-AM for 30 minutes and washed three times. Mixtures of T2 cells and CTL264 were incubated for 4 hours. 100 μL supernatants were transferred to a 96-well flat-bottom microtiter plates to read fluorescence (538 nm) to measure calcein release due to cell lysis. Surprisingly, we found that luteolin significantly inhibited CTL cytotoxicity against 264-pulsed T2 target cells in a concentration dependent manner (FIG. 2).

EXAMPLE 3

Figure 3:
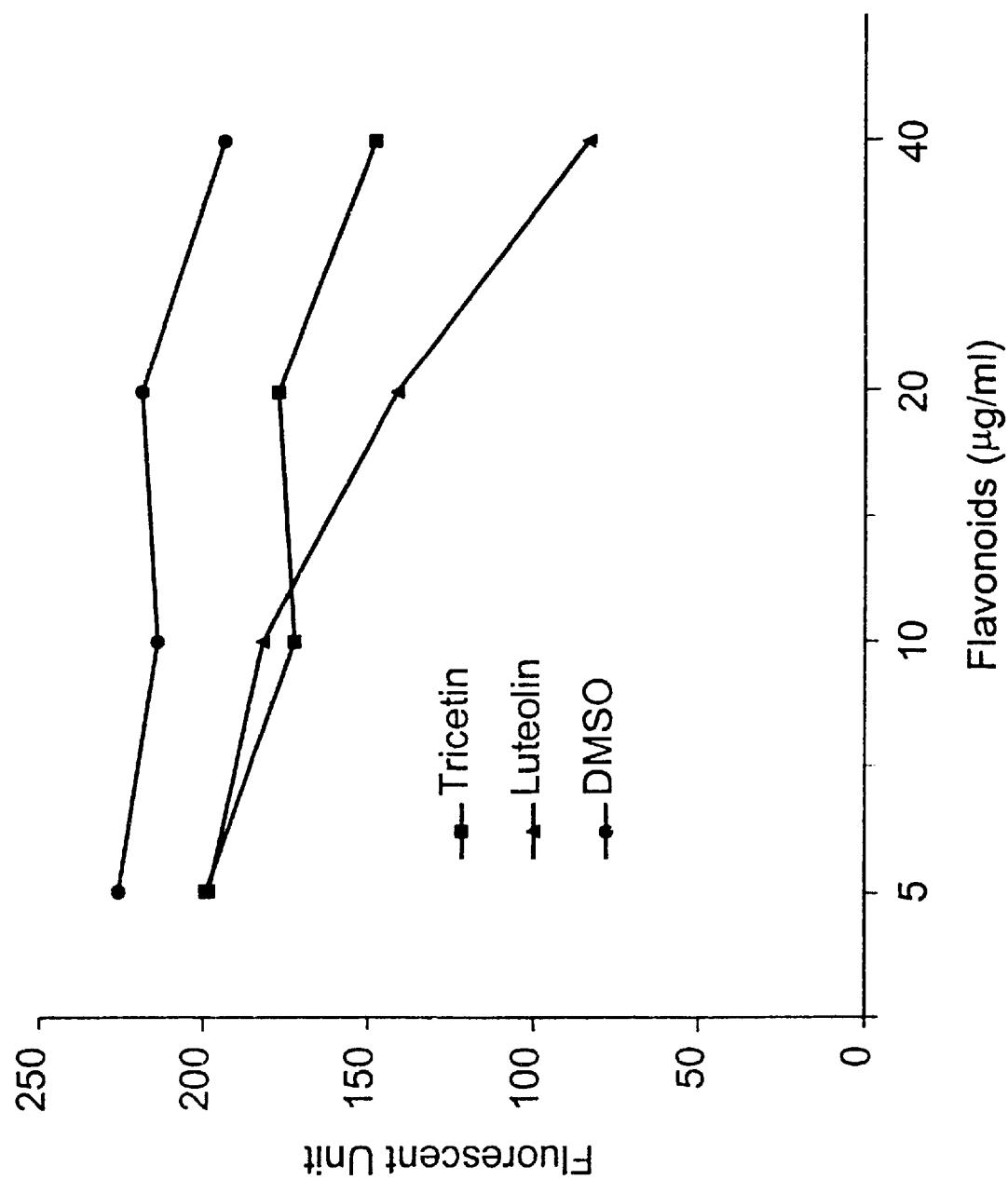

The spontaneous calcein release in cytotoxic T Lymphocytes was determined by incubation of targets in RPMI-10. The maximal calcein release was determined by incubation of targets in Triton X-100. Data are reported as the mean of triplicate determinations. FIG. 3 shows the inhibition of calcein release by 3-deoxyflavonoids luteolin and tricetin.

EXAMPLE 4

The effect of Luteolin treatment in chronic Type I (BBWor) diabetic rats was examined. In this study, lean male diabetic rats were randomly assigned to 3 treatment groups (3–4 rats/group). Each group received either: (1) 3 mg dose of luteolin intragastrically; (2) a subcutaneous injection of PZI insulin (0.9–1.2 mU/day); or (3) no treatment. Blood glucose was evaluated from time 0 through 6 hours. The data was expressed as average blood glucose relative to time post treatment.

The rats that received a single injection of insulin showed a 75% decrease in blood glucose levels (415 to 112 mg/dl) within 6 hours of injection. This response was fully consistent with our prior work in the Type 1 (BBWor) rat model. Rather remarkably, diabetic rats that received Luteolin showed a 31% drop in blood glucose levels (445 to 307 mg/dl) in 6 hours. In comparison, there was no reduction in the hyperglycemic state in the control group over the same interval (414 to 404 mg/dl). Thus, a single 3 mg dose of luteolin was able to reduce hyperglycemia within 6 hours as much as 31% in insulin-dependent diabetic (Type I BBWor) rats.

EXAMPLE 5

Luteolin was also evaluated for its effect to reduce hyperglycemia in chronic Type 2 diabetic rats. In this study, the dose and frequency of Luteolin treatment was increased to compensate for the enhanced metabolism of the obese rat. First, a 24 hour baseline study was performed on 9 chronic Type 2 rats. No significant change was observed in hyperglycemia over this 24 hour period of analysis in the diabetic rats. These same rats were randomly assigned to 3 groups and given 50, 150 and 250 mg doses of Luteolin at three times during the 24 hr period (11 AM, 2 PM and 8 PM). Blood glucose analysis was evaluated every 2 hours.

Figure 4:
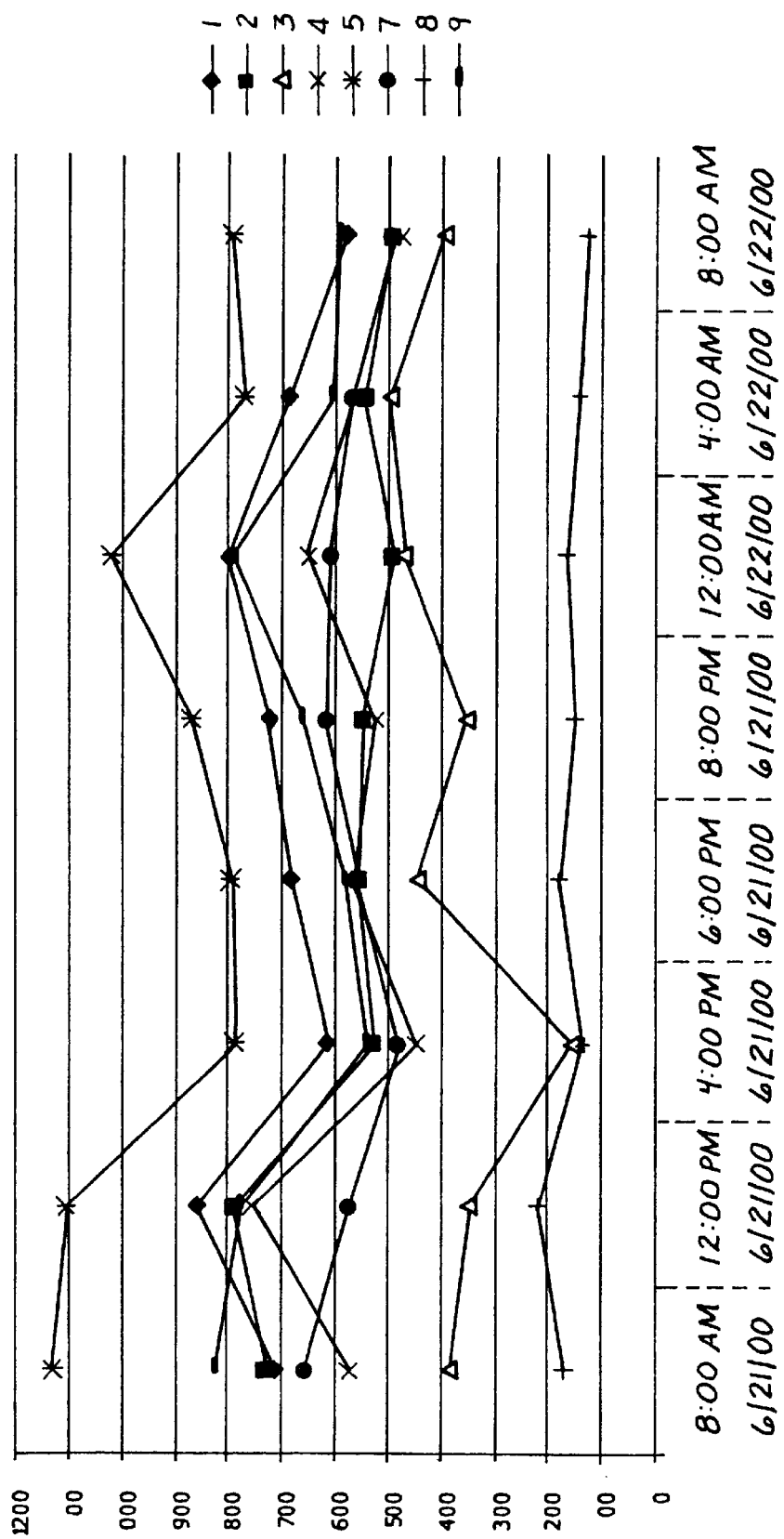

FIG. 4 shows the dose effects of Luteolin on diabetic Type II rats. Rats that received the lowest dose of 50 mg three time a day (150 mg total) showed a 10.2% decrease in blood glucose levels within 24 hr period of treatment. In comparison, rats treated an intermediate dose of 150 mg (450 mg total) showed a 22.9% drop in blood glucose. Rats in the third group that received the highest dose of 250 mg (750 mg total) showed the greatest change in glucose, a 27.7% decrease. Interestingly, the intermediate dose given to one rat reduced its blood glucose 52% (777 to 372 mg/dl) within 18 hr of treatment. Unfortunately, that animal died sometime before the 24 hr time point as a result of an accidental perforation of the esophagus during the administration of drug. These results demonstrate that Luteolin treatment markedly reduced hyperglycemia in the Type 2 diabetic rats 10–28% over a 24 hour period, and that these observations were dose-dependent.

EXAMPLE 6

In this example, the dose of luteolin was standardized to 50 mg three times per day in the same group of Type II BBZDR rats from Example 5 over an extended period of treatment of two weeks. This change in protocol resulted in further drop in blood glucose. The data was expressed for each rat as a percentage change in blood glucose level relative to each individual pre-treatment level.

Figure 5:
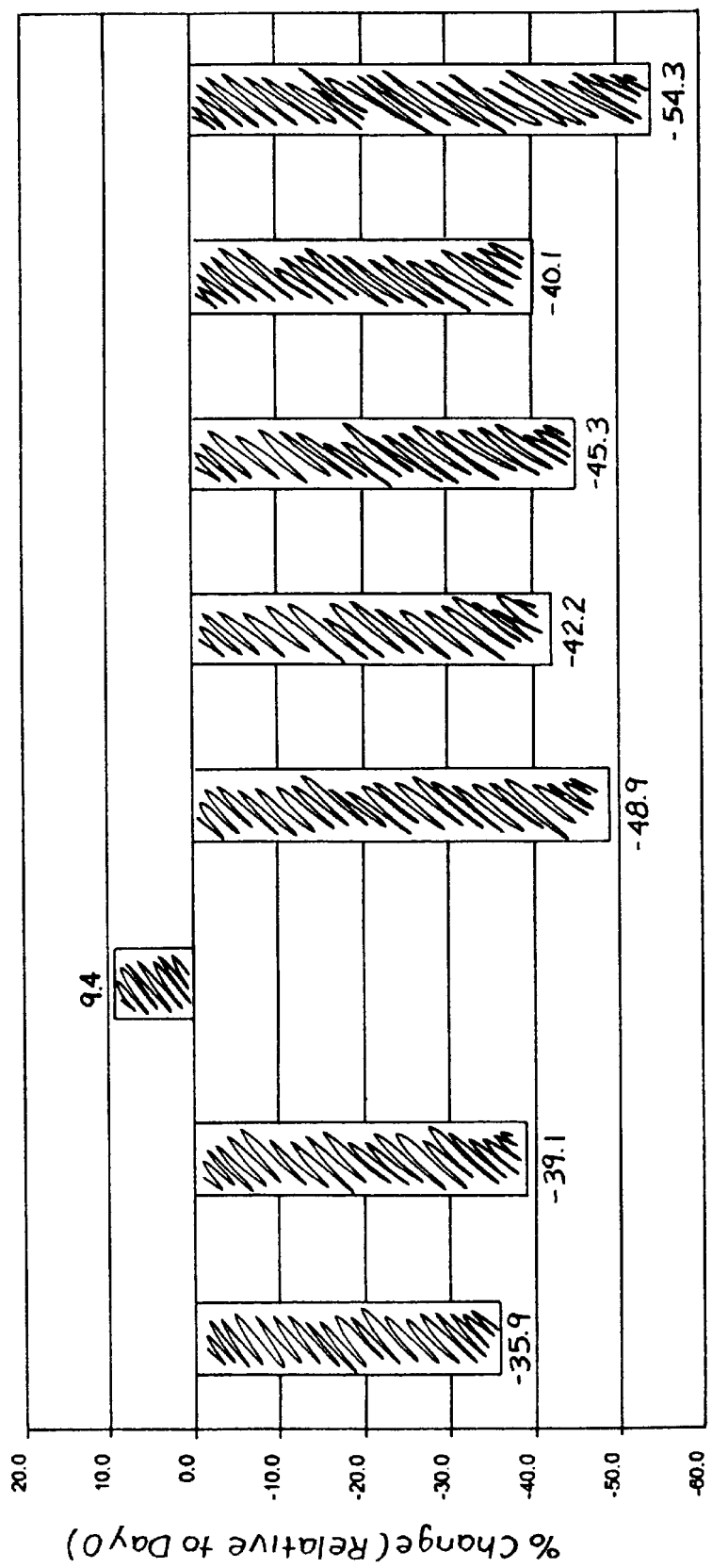

In FIG. 5, nearly all of the obese Type II (BBZDR) diabetic rats treated with 50 mg (three times per day) for two weeks showed decreased blood glucose levels (range: 36% to 54%), excluding one rat (#3). An esophagial fistula discovered at necropsy in the #3 rat showing a 9.3% increase in blood glucose likely prohibited effective dosing and response to treatment. Overall, blood glucose levels dropped an average of 41.1% (660 to 389 mg/dl) in the Type 2 diabetic rats.

EXAMPLE 7

Figure 6:
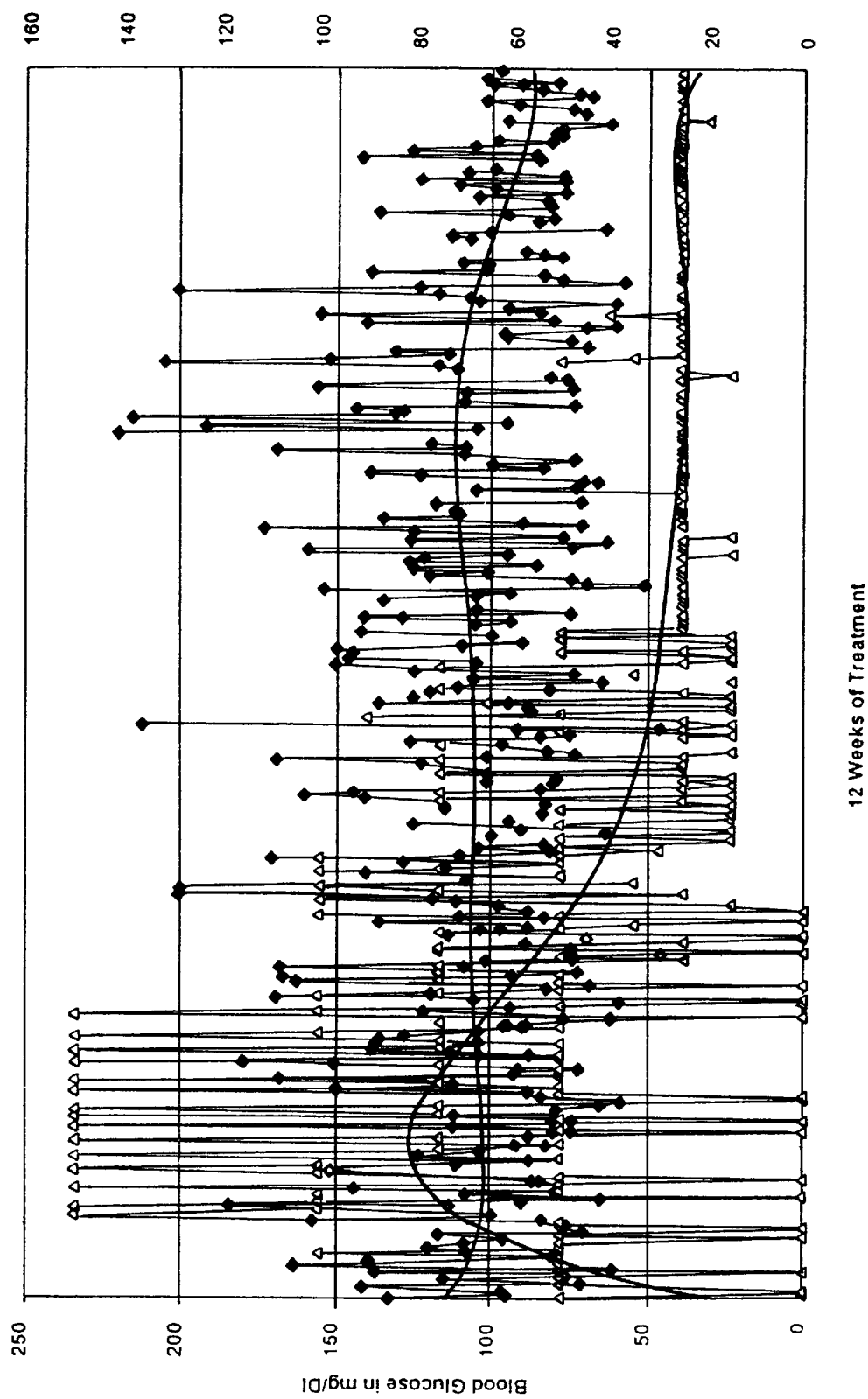

A 7 year old male with Type I diabetes antibodies was taking prophylactic insulin (NPH 2 units every night) since he was two years old. At 7 years and 4 months the child became symptomatic with blood glucose of 260 mg/dL and began taking 4 units of NPH every night to control blood glucose. After approximately 45 days of therapy with the insulin, the patient was given 75–150 mg of luteolin powder (75% luteolin, 25% rutin) sublingually four times a day in lieu of insulin. No insulin was required to maintain an average blood glucose of approximately 105 mg/dl. After approximately 20 days of luteolin powder (75% luteolin, 25% rutin) treatment, the dose of luteolin powder (75% luteolin, 25% rutin) was progressively reduced to 25 mg powder (75% luteolin, 25% rutin) four times a day with continued blood glucose control and improvement of glucose tolerance. The patient's blood was collected and analyzed for comprehensive metabolic enzymes including liver function, lipids, and glycated hemoglobin (HbA1c). All enzymes systems were normal and the HbA1c was 8.0. After 90 days of luteolin treatment at 25 mg powder (75% luteolin, 25% rutin) four times per day, the child had no observed blood glucose concentrations above 125 mg/dl with an average blood glucose concentration of 95 mg/dl and an $HbA_1c$ of 6.3. Luteolin (75% luteolin, 25% rutin) treatment and blood glucose concentrations are shown in FIG. 6.

EXAMPLE 8

Figure 7:
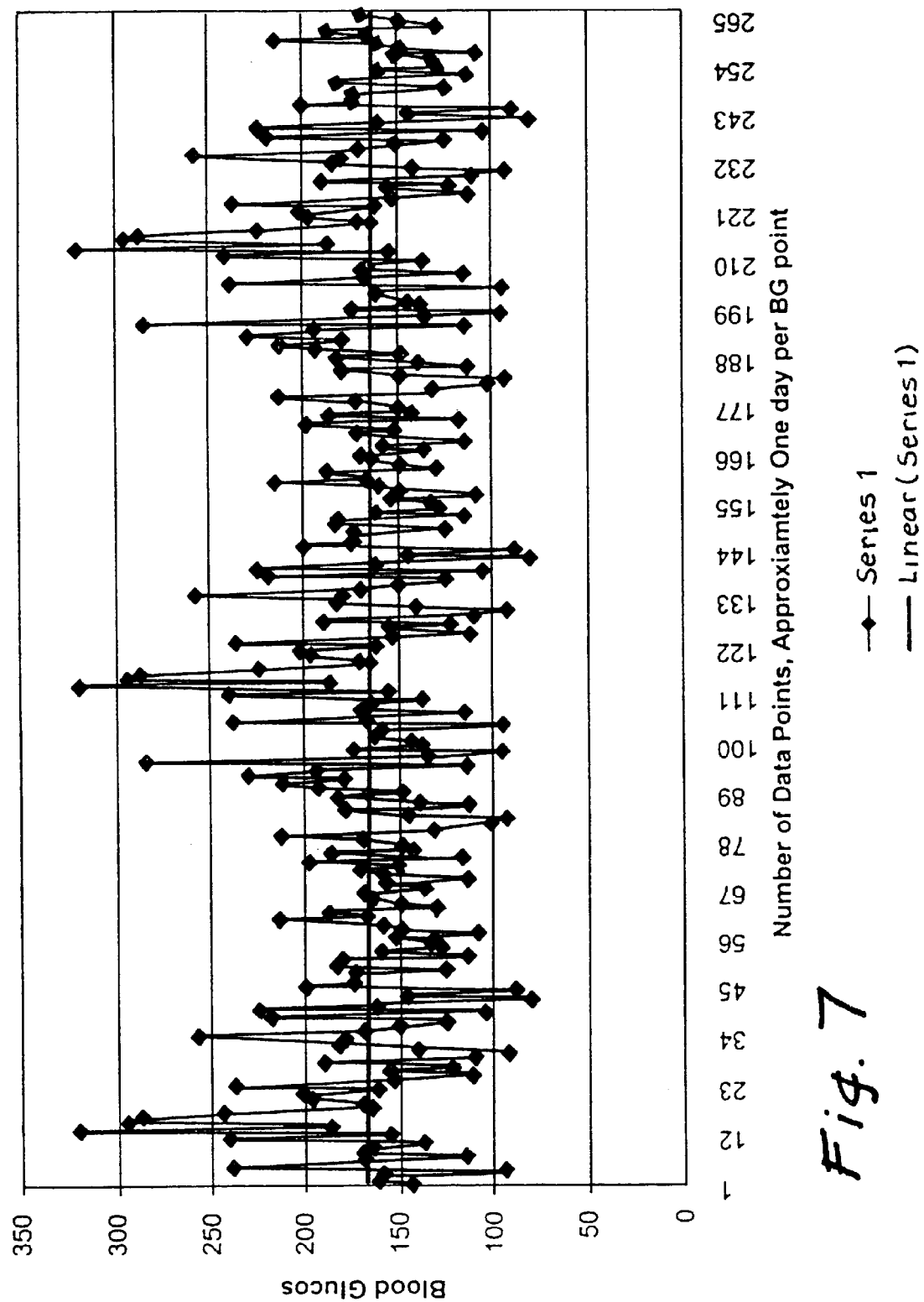
Figure 8:
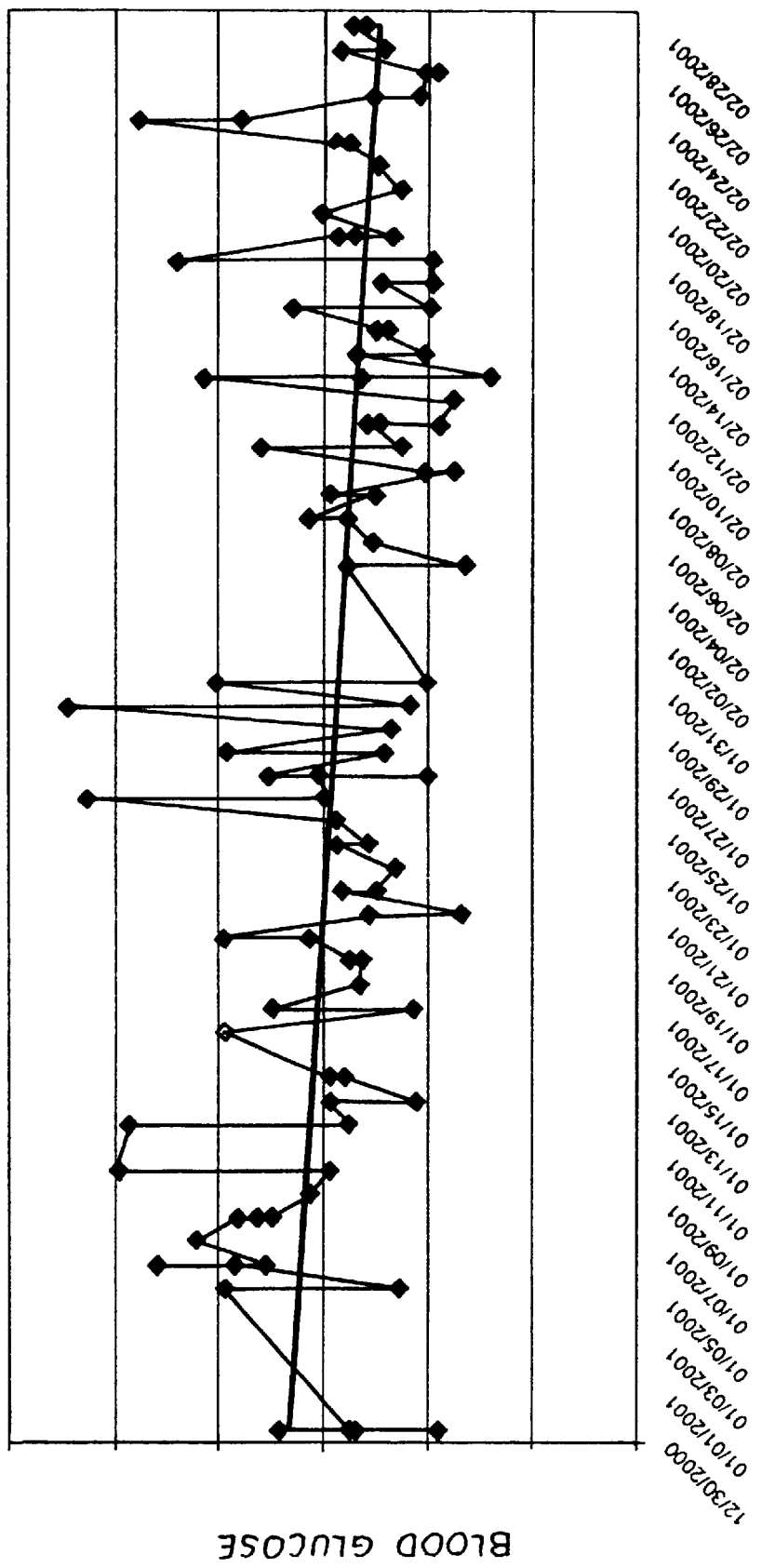

A 69 year old Caucasian male with Type II diabetes was medicated with Glucotrol XL 2×/day @ 10 mg, Actos 45 mg 1/day, Glucophage 1000 mg 2×/day. His average blood glucose for over one year was approximately 170 mg/dl. His blood glucose data for the previous year is shown in FIG. 7. The patient was given a composition described in Example 12 three times per day. The blood glucose of the patient was measured periodically as shown in FIG. 8. The data show a consistent drop in blood glucose over a period of approximately 60 days, which was not achieved using state-of-the-art prescription medications.

EXAMPLE 9

A 47 year old 145 pound Caucasian female with a history of 15 years of multiple sclerosis was in acute flare-up mode complaining of extreme pain in the eyes and extremities. The patient was medicated with beta interferon as directed by her physician. The patient was given 100 milligrams of luteolin powder (45% luteolin, 55% rutin) sublingually four times per day. The subject noted changes in her symptoms of neuropathy within a short period of time which is consistent with rapid sublingual or buccal absorption. Within 24 hours her symptoms were reduced by approximately 50% and within 72 hours she was symptom free for the duration of her 14 days of treatment with 100 mg of luteolin powder (45% luteolin, 55% rutin) four times a day. Upon withdrawal of luteolin (45% luteolin, 55% rutin), the subject experienced a relapse of multiple sclerosis symptoms within 5 days. She was then treated with 250 mg of luteolin powder (45% luteolin, 55% rutin) four times a day for one day and 100 mg of luteolin powder (45% luteolin, 55% rutin) per day continuously thereafter and observed remission of MS symptoms continuing for thirty days.

EXAMPLE 10

A 32 year old Caucasian male with a 10 year history of fibromyalgia induced by an severe automobile accident was unsuccessfully treated with anti-inflammatory compounds and pain killers. His joint pain exceeded his tolerance to physically work and he often remained on bed rest unable to move without severe pain. The subject was given 50 milligrams of luteolin powder (75% luteolin, 25% rutin) three times per day and he observed within two weeks that his symptoms were reduced dramatically and he was able to return to work. He no longer required pain medication and has not experienced a return of his symptoms.

EXAMPLE 11

The following composition depicts a typical formulation for alleviation of autoimmune disorders. The composition for each disorder may vary and not to be construed as fixed.

| β-Carotene | 6000 | IU |
|---|---|---|
| Retinyl Palmitate | 6000 | IU |
| Ascorbic Acid | 375 | mg |
| Ascorbyl Palmitate | 25 | mg |
| Cholecalciferol | 400 | IU |
| TPGS | 500 | mg |
| Phytonadione | 150 | mcg |
| Thiamin | 15 | mg |
| Riboflavin | 15 | mg |
| Niacin | 15 | mg |
| Niacinamide | 1450 | mg |
| Pyridoxin HCl | 22.5 | mg |
| Pyridoxal-5-Phosphate | 2.5 | mg |
| Folic Acid | 800 | mcg |
| Cyanocobalamin | 60 | mcg |
| Biotin | 3 | mg |
| Pantothenic Acid | 100 | mg |
| Calcium | 200 | mg |
| Iodine (KI) | 150 | mcg |
| Magnesium | 500 | mg |
| Zinc | 15 | mg |
| Selenium | 300 | mcg |
| Copper | 2 | mg |
| Manganese | 5 | mg |
| Chromium Picolinate | 400 | mcg |
| Molybdenum | 100 | mcg |
| Boron | 3 | mg |
| Silica | 10 | mg |
| Vanadyl Sulfate | 5 | mg |
| Choline Bitartrate | 50 | mg |
| Citrus Bioflavonoid Conc. | 500 | mg |
| Lipoic Acid | 50 | mg |
| Lutein | 3 | mg |
| 3-Deoxyflavonoid | 25 | mg |
| Lycopene | 2 | mg |
| N-Acetyl Cysteine | 200 | mg |
| Taurine | 500 | mg |
| 4-Carboxy-2-thiazolidone | 100 | mg |
| PEG-400 | 25 | mg |

A tablet composition for oral administration was prepared comprising the following ingredients

| Vitamin C (as ascorbic acid & calcium ascorbate) | 65 | mg |
|---|---|---|
| Vitamin D (as cholecalciferol) | 50 | IU |
| Vitamin E (as dl-alpha tocopheryl acetate) | 5 | IU |
| Niacin (as niacinamide) | 10 | mg |
| Biotin | 100 | mcg |
| Calcium (as calcium carbonate) | 160 | mg |
| Chromium (as chromium polynicotinate) | 100 | mcg |
| Vanadium (as vanadyl sulfate) | 10 | mcg |
| 3-Deoxyflavonoid (50% luteolin, 50% rutin) | 25 | mg |
| Microcrystalline Cellulose | 35 | mg |
| Croscarmellose Sodium | 7 | mg |
| Stearic Acid | 10.5 | mg |
| Magnesium Stearate | 3.2 | mg |
| Silicon Dioxide | 1.8 | mg |
| Opadry NS Y-40-19133 | 3.5 | mg |

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process and/or process step or steps, while remaining within the scope of the present invention. Accordingly, the scope of the invention should therefore be determined with reference to the appended claims, along with the full range of equivalents to which those claims are entitled.

What is claimed is:

1. A composition comprising 5-Hydroxy-3',4',7-tricarboxymethyloxyflavone.

2. A composition comprising 6,7 Methylenedioxy-3',4',5-trihydroxyflavone.

3. A composition comprising 7,8 Methylenedioxy-3',4',5-trihydroxyflavone.

4. A composition comprising 6,7-Carbonyloxy-3',4',5-trihydroxyflavone.

5. A composition comprising 3',4'-Carbonyloxy-5,7-dihydroxyflavone.

6. A composition comprising 3',5,7-Trihydroxyflavone-4'-phosphate.

7. A composition comprising 3',5,7-Trihdroxy-4'-(2-amino-1-carboxypropyloxy)flavone.

8. A method far inhibiting T-lymphocyte activity in a human or veterinary patient, said method comprising the step of administering to the patient, in an amount that is effective to inhibit T-lymphocyte activity, a compound having the formula:

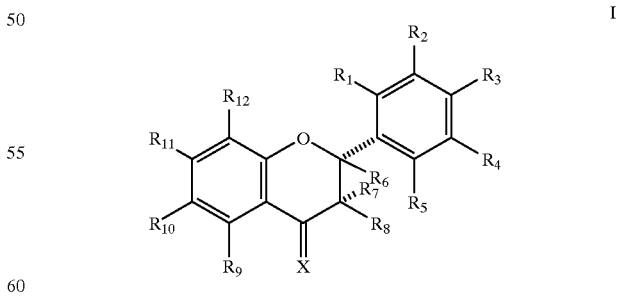

Wherein,
X is selected from O and S;
$R_1$ through $R_5$ and $R_9$ through $R_{12}$ are selected from H, OH, SH, Sme, Halogen, Alkyl, Amino, Cyano, Carboxyl, Carboxyalkyl, Carboxamide, alkoxycarbonyl, O-Hydroxyalkyl, CF3, O-Alkyl, O-SO3H, O-SO2H, O-PO3H, O-Glycoside, O-Glucoronide and O-Amino Acid, including O—CO-A-(CH2)n-NR'R", where A is Phenyl, substituted phenyl or absent; n is 0 through 5; R' and R" are selected from H, lower alkyl, hydroxyalkyl, aminoalkyl, mono and dialkylaminoalkyl, carboxyalkyl or R' and R" may combine to form a cyclic ring, optionally substituted with a O, S, NH or N-Alkyl and the methylene adjacent to the nitrogen may be optionally substituted with a amino alkyl, carboxy or carboxyalkyl group and O—CO—NH—(CH2)m-CH—(NH2)COOH, where m is 1 through 4;

R6 and R7 are H or may combine to form a doublebond;

R8 is selected from H, Halogen, Alkyl, Amino, Cyano, Carboxyl, Carboxyalkyl, Carboxamide, alkoxycarbonyl and CF3. Furthermore, when R1 through R5 and R9 through R12 are OH, SH or amino and are present on adjacent ring carbons then they may be combined through a methylene (—O—CH2-O—) or a carbonyl (—O—CO—O—, —O—CO—NH— or —S—CO—NH—) group to form a cyclic ring;

wherein the compound is administered in combination with Rutin, a congener of Rutin or derivative of Rutin.

9. A method according to claim 8 wherein the method is carried out for the purpose of treating diabetes or stabilizing the patient's blood glucose levels and wherein the compound is not luteolinthe 5 glucoside of luteolin, the 7 glucoside of luteolin, or apigenin.

10. A method according to claim 8 wherein the method is carried out for the purpose of treating Amyotrophic Lateral Sclerosis and wherein the compound is not luteolin, genistein, or daidzein.

11. A method according to claim 8 wherein the wherein the Rutin, congener of Rutin or derivative of Rutin comprises isoquercitrin.

12. A method according to claim 8 wherein a) the compound and b) the Rutin, congener of Rutin or derivative of Rutin are administered in a weight ratio of about 50%/50%.

13. A method according to claim 8 wherein a) the compound and b) the Rutin, congener of Rutin or derivative of Rutin are administered in a weight ratio of about 75%/25%.

14. A method according to claim 8 wherein a) the compound and b) the Rutin, congener of Rutin or derivative of Rutin are administered in a weight ratio in the range of about 50%/50% to about 75%/25%.

15. A method according to claim 12 wherein a) the compound and b) the Rutin, congener of Rutin or derivative of Rutin are administered in a weight ratio in the range of about 50%/50% to about 75%/25%.

16. A method according to claim 8 wherein the compound undergoes first pass metabolism when absorbed through the gastric and/or intestinal mucosa and wherein the compound is administered so as to be substantially absorbed by a route other than through the gastric and/or intestinal mucosa.

17. A method according to claim 16 wherein the compound is administered so as to be substantially absorbed via the patient's sublingual mucosa.

18. A method according to claim 16 wherein the compound is administered so as to be substantially absorbed via the patient's buccal mucosa.

19. A method according to claim 16 wherein the compound is administered so as to be substantially absorbed via the patient's rectal mucosa.

20. A method according to claim 16 wherein the compound is administered so as to be substantially absorbed via the patient's nasal mucosa.

21. A method according to claim 16 wherein the compound is administered so as to be substantially absorbed via the patient's sublingual mucosa.

22. A method according to claim 16 wherein the compound administered so as to be substantially absorbed through the patient's skin.

23. A method according to claim 16 wherein the compound is administered by injection.

24. A method according to claim 8 wherein R10 and R12 are OH.

25. A method according to claim 8 wherein the compound is 6,7 Methylenedioxy-3',4',5-trihydroxyflavone.

26. A method according to claim 8 wherein the compound is 7,8 Methylenedioxy-3',4',5-trihydroxyflavone.

27. A method according to claim 8 wherein the compound is 6,7-Carbonyloxy-3',4',5-trihydroxyflavone.

28. A method according to claim 8 wherein the compound is 3',4'-Carbonyloxy-5,7-dihydroxyflavone.

29. A method according to claim 8 wherein the compound is 3', 5,7-Trihydroxyflavone-4'-phosphate.

30. A method according to claim 8 wherein the compound is 3', 5,7-Trihdroxy-4'-(2-amino-1-carboxypropyloxy) flavone.

31. A method according to claim 8 wherein the compound is 5-Hydroxy-3',4',7-tricarboxymethyloxyflavone.

32. A method according to claim 8 wherein the compound is luteolin.

33. A method according to claim 8 wherein the rutin, a rutin congener or a rutin derivative is administered in an amount that is effective to enhance the efficacy or duration of action of the compound.

34. A method according to claim 8 wherein the compound is administered further in combination with genistein (5,7-Dihydroxy-3-(4-hydroxyphenyl)-4H-1benzopyran-4-one or 4',5,7-trihydroxyisoflavone).

35. A method according to claim 8 wherein the compound is administered further in combination with daidzein (7-Hydroxy-3-(4-hydroxyphenyl)-4H-1benzopyran-4-one OR 4',7-dihydroxyisoflavone).

36. A method for inhibiting T-lymphocyte activity in a human or veterinary patient, said method comprising the step of administering to the patient, in an amount that is effective to inhibit T-lymphocyte activity, a compound having the formula:

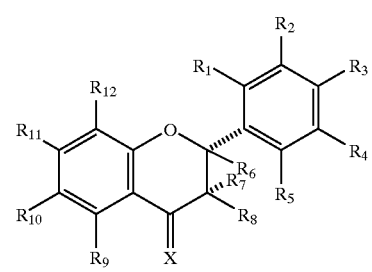

Wherein,

X is selected from O and S;

R1 through R5 and R9 through R12 are selected from H, OH, SH, Sme, Halogen, Alkyl, Amino, Cyano, Carboxyl, Carboxyalkyl, Carboxamide, alkoxycarbonyl O-Hydroxyalkyl, CF3, O-Alkyl, O-SO3H, O-SO2H, O-PO3H, O-Glycoside, O-Glucoronide and O-Amino Acid, including O—CO-A-(CH2)n-NR'R", where A is Phenyl, substituted phenyl or absent; n is 0 through 5; R' and R" are selected from H, lower alkyl, hydroxyalkyl, aminoalkyl, mono and dialkylaminoalkyl, carboxyalkyl or R' and R" may combine to form a cyclic ring, optionally substituted with a O, S, NH or N-Alkyl and the methylene adjacent to the nitrogen may be optionally substituted with a amino alkyl, carboxy or carboxyalkyl group and O—CO—NH—(CH2)m-CH.(NH2)COOH where m is 1 through 4;

R6 and R7 are H or may combine to form a doublebond;

R8 is selected from H, Halogen, Alkyl, Amino, Cyano, Carboxyl, Carboxyalkyl, Carboxamide, alkoxycarbonyl and CF3. Furthermore, when R1 through R5 and R9 through R12 are OH, SH or amino and are present on adjacent ring carbons then they may be combined through a methylene (—O—CH2-O—) or a carbonyl (—O—CO—O—, —O—CO—NH— or —S—CO—NH—) group to form a cyclic ring;

wherein the compound undergoes first pass metabolism when absorbed through the gastric and/or intestinal mucosa and wherein the compound is administered so as to be substantially absorbed by a route other than through the gastric and/or intestinal mucosa.

37. A method according to claim 36 wherein the method is carried out for the purpose of treating diabetes or stabilizing the patient's blood glucose levels and wherein the compound is not luteolin, the 5 glucoside of luteolin, the 7 glucoside of luteolin, or apigenin.

38. A method according to claim 36 wherein the method is carried out for the purpose of treating Amyotrophic Lateral Sclerosis and wherein the compound is not luteolin, genistein, or daidzein.

39. A method according to claim 36 wherein the method is carried out for the purpose of treating Amyotrophic Lateral Sclerosis and wherein the method comprises the step of administering a compound of the formula set forth in claim 36 in combination with another compound.

40. A method according to claim 36 wherein the compound is administered in combination with Rutin, a congener of Rutin or derivative of Rutin.

41. A method according to claim 40 wherein a) the compound of claim 36 and b) the Rutin, congener of Rutin or derivative of Rutin are administered in a weight ratio of about 50%/50%.

42. A method according to claim 36 wherein a) the compound of claim 36 and b) the Rutin, congener of Rutin or derivative of Rutin are administered in a weight ratio of about 75%/25%.

43. A method according to claim 36 wherein a) the compound of claim 36 and b) the Rutin, congener of Rutin or derivative of Rutin are administered in a weight ratio in the range of about 50%/50% to about 75%/25%.

44. A method according to claim 36 wherein the compound is administered so as to be substantially absorbed via the patient's sublingual mucosa.

45. A method according to claim 36 wherein the compound is administered so as to be substantially absorbed via the patient's buccal mucosa.

46. A method according to claim 36 wherein the compound is administered so as to be substantially absorbed via the patient's rectal mucosa.

47. A method according to claim 36 wherein the compound is administered so as to be substantially absorbed via the patient's nasal mucosa.

48. A method according to claim 36 wherein the compound is administered so as to be substantially absorbed via the patient's sublingual mucosa.

49. A method according to claim 36 wherein the compound administered so as to be substantially absorbed through the patient's skin.

50. A method according to claim 36 wherein the compound is administered by injection.

51. A method according to claim 40 wherein the Rutin, congener of Rutin or derivative of Rutin comprises isoquercitrin.

52. A method according to claim 36 wherein the compound is 6,7 Methylenedioxy-3',4',5-trihydroxyflavone.

53. A method according to claim 36, wherein the compound is 7,8 Methylenedioxy-3',4',5-trihydroxyflavone.

54. A method according to claim 36 wherein the compound is 6,7-Carbonyloxy-3',4',5-trihydroxyflavone.

55. A method according to claim 36 wherein the compound is 3',4'-Carbonyloxy-5,7-dihydroxyflavone.

56. A method according to claim 36 wherein the compound is 3', 5,7-Trihydroxyflavone-4'-phosphate.

57. A method according to claim 36 wherein the compound is 3',5,7-Trihdroxy-4'-(2-amino-1-carboxypropyloxy) flavone.

58. A method according to claim 36 wherein the compound is 5-Hydroxy-3',4',7-tricarboxymethyloxyflavone.

59. A method according to claim 36 wherein the compound is luteolin.

60. A method according to claim 36 wherein the compound is luteolin and wherein the method further comprises administering to the patient rutin, a rutin congener or a rutin analong in an amount that is effective to enhance the efficacy or duration of action of the luteolin.

61. A method according to claim 36 wherein the compound is administered in combination with genistein (5,7-Dihydroxy-3-(4-hycdroxyphenyl)-4H-1 benzopyran-4-one or 4',5,7-trihydroxyisoflavone).

62. A method according to claim 36 wherein the compound is administered in combination with daidzein (7-Hydroxy-3-(4-hydroxyphenyl)4H-1benzopyran-4-one OR 4',7-dihydroxyisoflavone).

63. A method for inhibiting T-lymphocyte activity in a human or veterinary patient, said method comprising the step of administering to the patient, in an amount that is effective to inhibit T-lymphocyte activity, a composition comprising 6,7 Methylenedioxy-3',4',5-trihydroxyflavone.

64. A method for inhibiting T-lymphocyte activity in a human or veterinary patient, said method comprising the step of administering to the patient, in an amount that is effective to inhibit T-lymphocyte activity, a composition comprising 7,8 Methylenedioxy-3',4',5-trihydroxyflavone.

65. A method for inhibiting T-lymphocyte activity in a human or veterinary patient, said method comprising the step of administering to the patient, in an amount that is effective to inhibit T-lymphocyte activity, a composition comprising 6,7-Carbonyloxy-3',4',5-trihydroxyflavone.

66. A method for inhibiting T-lymphocyte activity in a human or veterinary patient, said method comprising the step of administering to the patient, in an amount that is effective to inhibit T-lymphocyte activity, a composition comprising 5-Hydroxy-3',4',7-tricarboxymethyloxyflavone.

67. A method for inhibiting T-lymphocyte activity in a human or veterinary patient, said method comprising the step of administering to the patient, in an amount that is effective to inhibit T-lymphocyte activity, a composition comprising 3',4'-Carbonyloxy-5,7-dihydroxyflavone.

68. A method for inhibiting T-lymphocyte activity in a human or veterinary patient, said method comprising the step of administering to the patient, in an amount that is effective to inhibit T-lymphocyte activity, a composition comprising 3',5, 7-Trihydroxyflavone-4'-phosphate.

69. A method for inhibiting T-lymphocyte activity in a human or veterinary patient, said method comprising the step of administering to the patient, in an amount that is effective to inhibit T-lymphocyte activity, a composition comprising 3',5,7-Trihdroxy-4'-(2-amino-1-carboxypropyloxy) flavone.

70. A method according to any of claims 63–69 wherein the composition is administered in combination with Rutin, a congener of Rutin or derivative of Rutin.

71. A method according to any of claims 63–69 wherein the composition is administered in combination with Rutin, a congener of Rutin or derivative of Rutin, in a weight ratio of about 50%/50%.

72. A method according to any of claims 63–69 wherein the composition is administered in combination with Rutin, a congener of Rutin or derivative of Rutin, in a weight ratio of about 75%/25%.

73. A method according to any of claims 63–69 wherein the composition is administered in combination with Rutin, a congener of Rutin or derivative of Rutin, in a weight ratio in the range of about 50%/50% to about 75%/25%.

74. A method according to any of claims 63–69 wherein the composition is administered so as to be substantially absorbed via the patient's sublingual mucosa.

75. A method according to any of claims 63–69 wherein the composition is administered so as to be substantially absorbed via the patient's buccal mucosa.

76. A method according to any of claims 63–69 wherein the composition is administered so as to be substantially absorbed via the patient's rectal mucosa.

77. A method according to any of claims 63–69 wherein the composition is administered so as to be substantially absorbed via the patient's nasal mucosa.

78. A method according to any of claims 63–69 wherein the composition is administered so as to be substantially absorbed via the patient's sublingual mucosa.

79. A method according to any of claims 63–69 wherein the composition administered so as to be substantially absorbed through the patient's skin.

80. A method according to any of claims 63–69 wherein the composition is administered by injection.

81. A method according to any of claims 63–69 wherein the composition is administered in combination with genistein (5,7-Dihydroxy-3-(4-hydroxyphenyl)-4H-1benzopyran-4-one or 4',5,7-trihydroxyisoflavone).

82. A method according to claim 8 wherein the compound is administered further in combination with daidzein (7-Hydroxy-3-(4-hydroxyphenyl)-4H-1benzopyran-4-one OR 4',7-dihydroxyisoflavone).

83. A method according to any of claims 63–69 wherein the composition is administered in combination with isoquercitrin.

84. A method for inhibiting T-lymphocyte activity in a human or veterinary patient, said method comprising the step of administering to the patient, in an amount that is effective to inhibit T-lymphocyte activity, a first compound having the formula:

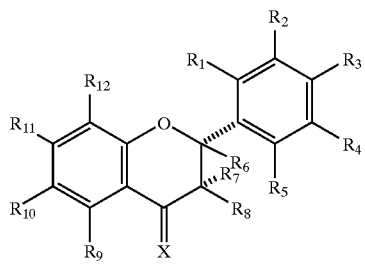

Wherein,

X is selected from O and S;

R1 through R5 and R9 through R12 are selected from H, OH, SH, Sme, Halogen, Alkyl, Amino, Cyano, Carboxyl, Carboxyalkyl, Carboxamide, alkoxycarbonyl, O-Hydroxyalkyl, CF3, O-Alkyl, O-SO3H, O-SO2H, O-PO3H, O-Glycoside, O-Glucoronide and O-Amino Acid, including O—CO—A-(CH2)n-NR'R", where A is Phenyl, substituted phenyl or absent; n is 0 through 5; R' and R" are selected from H, lower alkyl, hydroxyalkyl, aminoalkyl, mono and dialkylaminoalkyl, carboxyalkyl or R' and R" may combine to form a cyclic ring, optionally substituted with a O, S, NH or N-Alkyl and the methylene adjacent to the nitrogen may be optionally substituted with a amino alkyl, carboxy or carboxyalkyl group and O—CO—NH—(CH2)m-CH—(NH2)COOH, where m is 1 through 4;

R6 and R7 are H or may combine to form a doublebond;

R8 is selected from H, Halogen, Alkyl, Amino, Cyano, Carboxyl, Carboxyalkyl, Carboxamide, alkoxycarbonyl and CF3. Furthermore, when R1 through R5 and R9 through R12 are OH, SH or amino and are present on adjacent ring carbons then they may be combined through a methylene (—O—CH2-O—) or a carbonyl (—O—CO—O—, —O—CO—NH— or —S—CO—NH—) group to form a cyclic ring;

said method further comprising administering to the patient a second compound selected form the group consisting of genistein (5,7-Dihydroxy-3-(4-hydroxyphenyl)-4H-1 benzopyran-4-one or 4',5,7-trihydroxyisoflavone); and daidzein (7-Hydroxy-3-(4-hydroxyphenyl)-4H-1benzopyran-4-one OR 4',7-dihydroxyisoflavone.

85. A method according to claim 84 wherein the method is carried out for the purpose of treating diabetes or stabilizing the patient's blood glucose levels and wherein the first compound is not luteolin, the 5 glucoside of luteolin, the 7 glucoside of luteolin, or apigenin.

86. A method according to claim 84 the method is carried out for the purpose of treating Amyotrophic Lateral Sclerosis and wherein the first compound is not luteolin, genistein, or daidzein.

87. A method according to claim 84, wherein the method is carried out for the purpose of treating Amyotrophic Lateral Sclerosis and wherein the method comprises the step of administering a first compound of the formula set forth in claim 38 in combination with another first compound.

88. A method according to claim 84 the first compound is administered further in combination with Rutin, a congener of Rutin or derivative of Rutin.

89. A method according to claim 88 wherein a) the first compound of claim 84 and b) the Rutin, congener of Rutin or derivative of Rutin are administered in a weight ratio of about 50%/50%.

90. A method according to claim 88 wherein a) the first compound of claim 86 and b) the Rutin, congener of Rutin or derivative of Rutin are administered in a weight ratio of about 75%/25%.

91. A method according to claim 88 wherein a) the first compound of claim 36 and b) the Rutin, congener of Rutin or derivative of Rutin are administered in a weight ratio in the range of about 50/50% to about 75%/25%.

92. A method according to claim 84 wherein the first compound is administered so as to be substantially absorbed via the patient's sublingual mucosa.

93. A method according to claim 84 wherein the first compound is administered so as to be substantially absorbed via the patient's buccal mucosa.

94. A method according to claim 84 wherein the first compound is administered so as to be substantially absorbed via the patient's rectal mucosa.

95. A method according to wherein the first compound is administered so as to be substantially absorbed via the patient's nasal mucosa.

96. A method according to claim 84 wherein the first compound is administered so as to be substantially absorbed via the patient's sublingual mucosa.

97. A method according to claim 84 wherein the first compound administered so as to be substantially absorbed through the patient's skin.

98. A method according to claim 84 wherein the first compound is administered by injection.

99. A method according to claim 88 wherein the Rutin, congener of Rutin or derivative of Rutin comprises isoquercitrin.

100. A method according to claim 84 wherein the first compound is 6,7 Methylenedioxy-3',4',5-trihydroxyflavone.

101. A method according to claim 84 wherein the first compound is 7,8 Methylenedioxy-3',4',5-trihydroxyflavone.

102. A method according to claim 84 wherein the first compound is 6,7-Carbonyloxy-3',4',5-trihydroxyflavone.

103. A method according to claim 84 wherein the first compound is 3',4'-Carbonyloxy-5,7-dihydroxyflavone.

104. A method according to claim 84 wherein the first compound is 3',5,7-Trihydroxyflavone-4'-phosphate.

105. A method according to claim 84 wherein the first compound is 3',5,7-Trihdroxy-4'-(2-amino-1-carboxypropyloxy) flavone.

106. A method according to claim 84 wherein the first compound is 5-Hydroxy-3',4',7-tricarboxymethyloxyflavone.

107. A method according to claim 84 wherein the first compound is luteolin.

108. A method according to claim 84 wherein the first compound is luteolin and wherein the method further comprises administering to the patient rutin, a rutin congener or a rutin analong in an amount that is effective to enhance the efficacy or duration of action of the luteolin.

109. A method according to claim 84 wherein second compound is genistein (5,7-Dihydroxy-3-(4-hydroxyphenyl)-4H-1benzopyran-4-one or 4',5,7-trihydroxyisoflavone) in an amount that is effective to enhance the efficacy or duration of action of the first compound.

110. A method according to claim 36 wherein the second compound is daidzein (7-Hydroxy-3-(4-hydroxyphenyl)-4H-1benzopyran-4-one OR 4', 7-dihydroxyisoflavone) in an amount that is effective to enhance the efficacy or duration of action of the first compound.

* * * * *